(12) United States Patent
Chernajovsky et al.

(10) Patent No.: US 8,357,515 B2
(45) Date of Patent: Jan. 22, 2013

(54) LATENCY ASSOCIATED PROTEIN CONSTRUCT WITH AGGRECANASE SENSITIVE CLEAVAGE SITE

(75) Inventors: Yuti Chernajovsky, London (GB); Gillian Adams, London (GB)

(73) Assignee: Queen Mary & Westfield College, London (GB)

( * ) Notice: Subject to any disclaimer, the term of this patent is extended or adjusted under 35 U.S.C. 154(b) by 53 days.

(21) Appl. No.: 12/808,383

(22) PCT Filed: Dec. 17, 2008

(86) PCT No.: PCT/GB2008/004167
§ 371 (c)(1),
(2), (4) Date: Aug. 19, 2010

(87) PCT Pub. No.: WO2009/077755
PCT Pub. Date: Jun. 25, 2009

(65) Prior Publication Data
US 2010/0310515 A1 Dec. 9, 2010

(30) Foreign Application Priority Data
Dec. 17, 2007 (GB) .................................. 0724556.6

(51) Int. Cl.
*C12P 21/06* (2006.01)
*C12N 5/10* (2006.01)
*C07H 21/04* (2006.01)
*C07K 14/475* (2006.01)
*A61K 38/19* (2006.01)

(52) U.S. Cl. ...... 435/69.7; 435/69.5; 435/325; 435/243; 435/320.1; 536/23.4; 536/23.5; 530/351; 514/16.6; 514/16.8; 514/825

(58) Field of Classification Search .................. None
See application file for complete search history.

(56) References Cited

U.S. PATENT DOCUMENTS

| | | | |
|---|---|---|---|
| 4,103,002 A | 7/1978 | Hench | |
| 4,234,972 A | 11/1980 | Buscemi et al. | |
| 4,725,234 A | 2/1988 | Ethridge | |
| 5,074,916 A | 12/1991 | Hench | |
| 5,120,340 A | 6/1992 | Ducheyne et al. | |
| 5,314,474 A | 5/1994 | Helms et al. | |
| 5,679,338 A * | 10/1997 | Yeh et al. | 424/85.2 |
| 5,856,356 A | 1/1999 | Tsouderos et al. | |
| 6,482,444 B1 | 11/2002 | Bellantone et al. | |
| 6,569,466 B2 | 5/2003 | Ducheyne et al. | |
| 6,905,723 B2 | 6/2005 | Li | |
| 6,942,853 B2 * | 9/2005 | Chernajovsky et al. | 424/85.1 |
| 7,307,147 B2 * | 12/2007 | Chernajovsky et al. | 530/350 |
| 2004/0065228 A1 | 4/2004 | Kessler et al. | |
| 2006/0142413 A1 | 6/2006 | Zimmer et al. | |
| 2007/0122356 A1 | 5/2007 | Kessler et al. | |

FOREIGN PATENT DOCUMENTS

| | | |
|---|---|---|
| CN | 1559888 | 1/2005 |
| EP | 0626165 A1 | 11/1994 |
| EP | 08/02890 A1 | 10/1997 |
| EP | 1481696 A2 | 1/2004 |
| WO | 95/09131 A1 | 4/1995 |
| WO | 98/17236 A1 | 4/1998 |
| WO | 98/40320 A1 | 9/1998 |
| WO | 02/055098 A1 | 7/2002 |
| WO | 2004/071542 A1 | 8/2004 |
| WO | 2006/050829 A1 | 5/2006 |
| WO | 2007/020613 A1 | 2/2007 |
| WO | 2008/090533 A2 | 7/2008 |
| WO | 2008/014964 A2 | 9/2008 |

OTHER PUBLICATIONS

Hills et al. Identification of an ADAMTS-4 cleavage motif using phage display leads to the development of fluorogenic peptide substrates and reveals matrilin-3 as a novel substrate. J Biol Chem. Apr. 13, 2007;282(15)11101-9. Epub Feb. 20, 2007.*

Hill, R.G. et al. The influence of strontium-substitution in fluoroapatite glasses and glass-ceramics on nucleation. Journal of Non-crystalline Solids. (2004) 336(3), pp. 223-229.

Hayakawa, S. et al. Biomimetic deposition of calcium phosphates on oxides soaked in simulated body fluid. Journal of Non-Crystalline Solids. (2000) 263-264(1-2), pp. 409-415.

Rakovan, J. F. et al. Strontium in the Apatite Structure; strontiun fluorapatite and belovite-(Ce). The Canadian Mineralogist. (2000) 38, pp. 839-845.

Christoffersen, J. et al. Effects of strontium ions on growth and dissolution of hydroxyapatite and on bone mineral detection. Bone. (1997) 20(1), pp. 47-54.

Grynpas, M.D. et al. Strontium increases vertebral bone volume in rates at a low dose that does not induce detectable mineralization defect. Bone.(1996) 18(3), pp. 253-259.

Nielsen, S.P. The biological role of strontium. Bone. (2004) 35(3), pp. 583-588.

Barbara, A. et al. Normal matrix mineralization induced by strontium renelate in MC3T3-E1 Osteogenic cells. Metabolism: Clinical and Experimental. (2004) 53(4) pp. 532-537.

Delannoy, P. et al. Long term treatment with strontium renelate increases vertebral bone mass without deleterious effects in mice. Metabolism: Clinical and Experimental. (2002) 51(7), pp. 906-911.

Buehler, J. et al. Strontium renelate inhibits bone resorption while maintaining bone formation in alveolar bone in monkeys. Bone. (2001) 29(2), pp. 176-179.

Rokita, E et al. Bone minerlization after strontium and fluorine treatment in osteoporosis. Nuclear Instruments and Methods in Physics Research B. (1999) 158(1).

Hench, Bioactive Ceramics, in Bioceramics: Material Characteristics Versus In Vivo Behavior (P. Ducheyne & J. E. Lemons, Eds., 1988), pp. 54-71.

Warren, Clark & Hench, Quality Assurance of Bioactive glass.sup.(R) Powders, 23 J. Biomed. Mat. Res.-App. Biomat. 201 (1989).

Hench & West, The Sol-Gel Process, 90 Chem. Rev. 33 (1989).

(Continued)

*Primary Examiner* — David Romeo
(74) *Attorney, Agent, or Firm* — Pepper Hamilton LLP

(57) ABSTRACT

The present provides a fusion protein comprising a latency associated peptide (LAP) and a pharmaceutically active agent in which the LAP and the pharmaceutically active agent are connected by an amino acid sequence comprising an aggrecanase proteolytic cleavage site.

16 Claims, 8 Drawing Sheets

OTHER PUBLICATIONS

Figure 3:
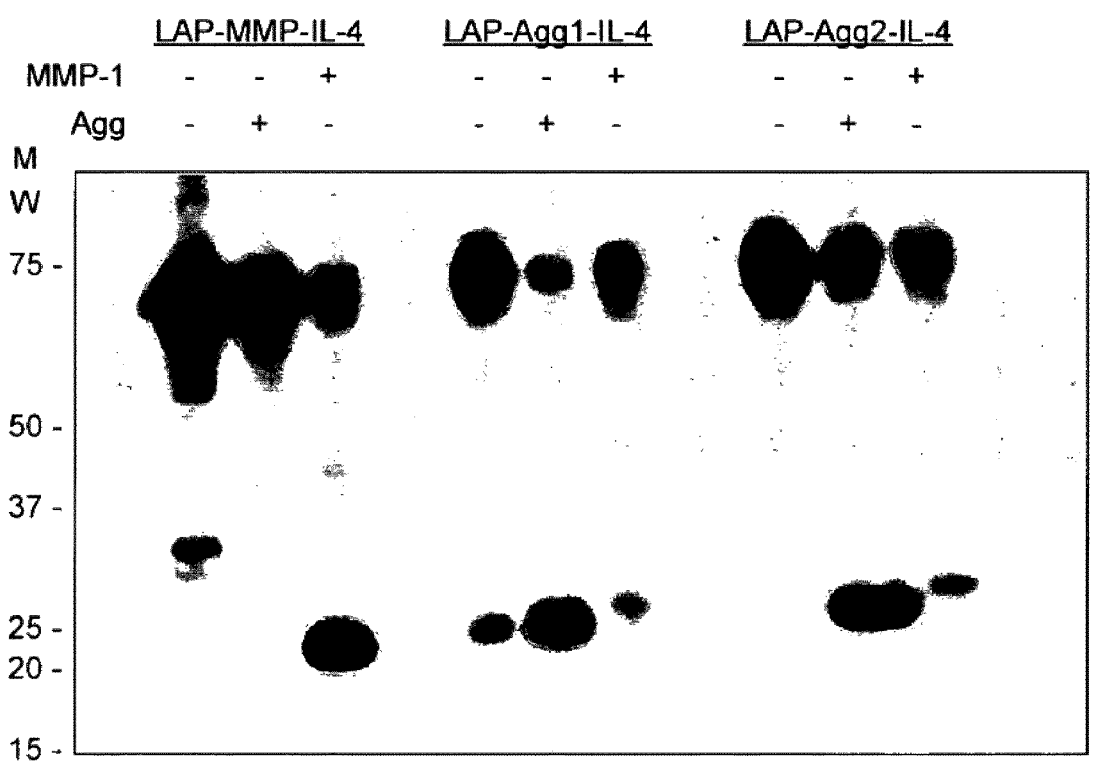

Kokubo, T., et al., Solutions able to reproduce in vivo surface-structure changes in bioactive glass-ceramic A-W, J. Biomed. Mater. Res., Jun. 1990; 24(6):721-734.

Shieh, H. S., et al., High resolution crystal structure of the catalytic domain of ADAMTS-5 (aggrecanase-2), J Biol Chem. Jan. 18, 2008;283(3):1501-7.

Vessillier, S., et al., Molecular engineering of short half-life small peptides (VIP, αMSH and y$_3$MSH) fused to latency-associated peptide results in improved anti-inflammatory therapeutics, Ann Rheum Dis. Jan. 2012;71(1):143-9. Epub Oct. 13, 2011.

Vessillier, S. et al., Latent cytokines: development of novel cleavage sites and kinetic analysis of their differential sensitivity to MMP-1 and MMP-3, Protein Engineering, Design & Selection: Peds, Dec. 2004;17(12):829-835.

Porter, S., et al., The Adamts Metalloproteinases, Biochemical Journal, Feb. 15, 2005;386(1):15-27.

* cited by examiner

FIG. 1

```
              1                                                           60
Hu TGF-β1    MPPSGLRLLRLLPLLPLLWLLV-LTPGPPAAGLSTCKTIDMELVKRKRIEAIRGQILSKLRLASPPSQGE-VP-PGP
Hu TGF-β2    MHYCVLSAFLILH    LVTVAL------SLSTCSTLDMDQFMRKRIEAIRGQILSKLKLTSPP---EDYPEPEE
Hu TGF-β3    MKMHLQRALVVLALLHFATVSL------SLSTCTTLDFGHIKKRVEAIRGQILSKLRLTSPP----EPTV-MTH
Ck TGF-β4    ----------------------------------------------------------------------------
Fg TGF-β5    MEV--------LWMLLVLLIV-LHLSSLANSLSTCKAVDMEEVRKRRIEAIRGQILSKLKLDKIPVDS-EK-MTV
                                        +                    + +++++++++++   +

61                                                          120
Hu TGF-β1    LPEAVLALYNSTRDRVAGESAEPE-PEP--------EADYYAKEVIRVLMV------ETHNEIYDKFKQSTHSIYMFF
Hu TGF-β2    VPPEVISIYNSTRDLL--QEKASR-RAAACERERSDEEYYAKEVYKIDMPPFFPS-ENAIPPTFYRPY-FRIVRF
Hu TGF-β3    VPYQVLALYNSTRELL--EEHGER-KEEGCTQENTESEYYAKEIHKFDMIQGLAE-HNELAVCPKGIT-SKVFRF
Ck TGF-β4    -----------M---DPMSIGPK---SCG-----------------------GSPW-RPP-GTAPWSIG-SR--RA
Fg TGF-β5    PSEAIF-LYNSTLE-VIREKATRE-EEEHVGHDQNIQDYYAKQVYRE----ESITELEDHEFKFK------F
                            +                              ++++

121                                                         180
Hu TGF-β1    NTSEL------RE-AVPEPVLLS-RAELRLLRLKL----KV-EQHVELYQ----KYSNNSWRYLSNRLLAPSDSPE
Hu TGF-β2    DVSA-------MEKNASNLV-KAEFRVFRLQNPK-ARVPEQRIELYQILKSKDLISPTQRYIDSKVVKTRAEGE
Hu TGF-β3    NVSS-------VEKNRTNLF-RAEFRVLRVPNPS-SKRNEQRIELFQILRP-DEHIAKQRYIGGKNLPTRGTAE
Ck TGF-β4    TASSSSCSTSSRVRAEVGGRALLHRAELRHLRQKAAADSAGTEQRLELYQGYG---NASWRYLHGRSVRATSDDE
Fg TGF-β5    NASHV-----RENVGMN-SLLH-HAELRMYK-KQTD---KNMDQRMELFW--KYQENGTTHSRYLESKYITPVTDQE
                    +        +       +  ++                              ++
```

```
                     200                       220                       240
Hu TGF-β1   WLSFDVTGVVRQWLSRGGEIEGFRLSAHCSG------DSRDNTLQVDIN-GFTTGR------RGDLATI----
Hu TGF-β2   WLSFDVTDAVHEWLHHKDRWLGFKISLHCPCCTFVSNKEELEARFA-GIDGTSTYTSGDQKTIKSTRK
Hu TGF-β3   WLSFDVTDTVREWLLRRESNLGLEISIHCPCHTFQP-NGDILENIHEVMEIKFK-GVDNEDDHGRGDLGRLK---K
Ck TGF-β4   WLSFDVTDAVHQWLSGSELIGVFKLSVHCPCEMGPG-HADEMRISIEGFEQQ---------RGDMQSIA---K
Fg TGF-β5   WNSFDVTKTVNEWLKRAEENEQFGLQPAGKG--------PTPQAKD----IDIEGFPAL-RGDLASL-SSK
             + ++++ +      + +    +                                  *            ++

260              ↓ 280                     300
Hu TGF-β1   ----HGMWRPFLLLMATPLERA-QK--LQSS---RHRRALDTNYCFSST--EKNCCVRQLYIDFRKDLGWKWIHEP
Hu TGF-β2   KNSGKT----PHLLLMLLPSYRL-ESQ---QTNRRKKRALDAAYCFRNV--QDNCCLRPLYIDFKRDLGWKWIHEP
Hu TGF-β3   QKDNN---N-PHLILMMIPPHRL-DNPGQGGQ--RKKRALDTNYCFRNL--EENCCVRPLYIDFRQDLGWKWVHEP
Ck TGF-β4   -KHRR----V-PYVLAMALPAERANE---LHSA---RRRRDLDTDYCFGPGTDEKNCCVRPLYIDFRKDLQWKWIHEP
Fg TGF-β5   ENT-----KPYL--MITSMPAERIDTVT SS---RKKRGVGQEYCFGNN--GPNCCVKPLYINFRKDLGWKWIHEP
             +        +                 +        +**  +  +  ++  +++  +  +  ++  +++ + +++

320                340                 360               380                390
Hu TGF-β1   KGYHANFCLGPCPYIWSLDTQYSKVIALYNQHNPGASAAPCCVPQALEPLPIVYYVGRKPKVEQLSNMIVRSCKCS
Hu TGF-β2   KGYNANFCAGACPYLWSSDTQHSRVLSLYNTINPEASASPCCVSQDLEPLTILYYIGKIPKIEQLSNMIVKSCKCS
Hu TGF-β3   KGYYANFCSGPCPYLRSADTTHSTVLGLYNTLNPEASASPCCVPQDLEPLTILYYIGRIPKVEQLSNMVKSCKCS
Ck TGF-β4   KGYMANFCMGPCPYIWSADTQYIKVLALYNQHNPGASAAPCCVPQILDPLPIIYYVGRNVRVEQLSNMVRACKCS
Fg TGF-β5   KGYEANYCLGNCPYIWSMDTQYSKVLSLYNQHNPGASISPCCVPDVLEPLPIIYYVGRIAKVEQLSNMVVRSCNCS
             +++ ++ +  ++++  + ++    + ++++ +++++ + ++++   +++ + ++ +   ++++++++   + +*
```

FIG. 1 CONT'D

| Phage Code | Peptide Sequence | Avg. % Cleaved |
|---|---|---|
| D04 | ----MMF-KGQR-VERVLT | 99.7 |
| B05 | ---HNFF-RQRETYMVF-- | 99.6 |
| B07 | --NWQFFQ-AKRSVAY--- | 99.5 |
| D03 | ----LEL-ESN-SVIMRWP | 99.4 |
| C02 | --DYMEV-RRQMSMQM--- | 99.4 |
| F03 | ---ALEM-RAAD-VEYHF- | 99.3 |
| D01 | VEHLMEVQRKT-TW----- | 99.2 |
| C05 | ---GVEV-KRQLSYHYM-- | 99.1 |
| B08 | ----QELVGANIETYML-- | 99.0 |
| C06 | --QQMEVSRYV-QMKW--- | 98.9 |
| F05 | ---LQSF-RQAP-VDIWW- | 98.9 |
| H04 | ----QEL-RGKISIQPFK- | 98.9 |
| E03 | ---QQEYMSGQYDIIF--- | 98.8 |
| D07 | ---SMEFA-ATVTSTFE-- | 98.7 |
| C07 | ---EQQL-KGRQTHIII-- | 98.5 |
| B02 | ----MEL-KGQ-TDMFYII | 98.5 |
| F01 | ---GAYAV-GRWSYVDA-- | 98.3 |
| B01 | ---GQFATSPKITHK--- | 98.2 |
| B06 | --DVQFF-RGV-TAVIR-- | 98.0 |
| A05 | ----HEA-RTVSTTYLML- | 98.0 |
| C04 | ---YMEN-RGSTVFFN-- | 97.9 |
| F06 | ----QELIGSY-SVMPTN- | 97.9 |
| E01 | -HYYMEATRDIEMV----- | 97.9 |
| A06 | ----NEAHSSGITMLR-- | 97.8 |
| H01 | -DHPMEF-RSKITMK---- | 97.8 |
| A01 | --TFAEM-KGTVSYAL--- | 97.7 |
| F04 | -GVHMESMRRY-TVI---- | 97.7 |
| E05 | ---FQEYTG----TYDIMDP | 97.6 |
| A04 | -FQAVEASK-TLHEW---- | 97.6 |
| D02 | ---YLETSRTY-TTVWP-- | 97.5 |
| F08 | -TDYLEV-RSQPITY---- | 97.2 |
| B03 | -TFEQEV-RAPN-ISW--- | 97.1 |
| B04 | ---PQEVQGIAVEWV---- | 96.9 |
| F10 | ----AEA-KAS-TLHVYLM | 96.8 |
| D09 | --DYMEVVGNKISYI---- | 96.7 |
| F09 | --VIMEAV-GRKTILQ--- | 96.5 |
| D10 | --FQAEAARAV-TYSS--- | 96.5 |
| F07 | -EDYVYV-KDVGTTN---- | 96.4 |
| A08 | ----QEY-KAHHSYKLMS- | 96.2 |
| C03 | ---YNEY-RATPTFAVV-- | 95.8 |
| H03 | -----EYFHANTTRIVQS- | 95.4 |
| G02 | ---ALFASRFI-SWDIN-- | 95.3 |
| C01 | ----WEAVAAP--IMHTWV | 94.3 |
| E02 | ---FQEL-KAAETWM--- | 94.1 |
| F02 | --NTLYAV-APPVIYV--- | 90.4 |
| G01 | -FQPYEVQRIT-TVM---- | 89.9 |
| A02 | --KPMESGRRT-TVYY--- | 88.5 |
| G05 | ----MEF-KGALQYRLQP- | 82.9 |
| H02 | ---PQEV-KQARKWIIE-- | 79.4 |
| A07 | -YRQQEVKRHIQIV----- | 34.2 |

E-[AFVLMY]-X(0,1)-[RK]-X(2,3)-[ST]-[VYIFWMLA]

FIG. 2

FIG. 4

```
              9           18          27          36          45          54
5' ATG CCG CCC TCC GGG CTG CGG CTG CTG CCG CTG CTG CTA CCG CTG CTG TGG CTA
   --- --- --- --- --- --- --- --- --- --- --- --- --- --- --- --- --- ---
   Met Pro Pro Ser Gly Leu Arg Leu Leu Pro Leu Leu Leu Pro Leu Leu Trp Leu 63          72          81          90          99         108
   CTG GTG CTG ACG CCT GGC CCG CCG GCC GCG GGA CTA TCC ACC TGC AAG ACT ATC
   --- --- --- --- --- --- --- --- --- --- --- --- --- --- --- --- --- ---
   Leu Val Leu Thr Pro Gly Pro Pro Ala Ala Gly Leu Ser Thr Cys Lys Thr Ile 117         126         135         144         153         162
   GAC ATG GAG CTG GTG AAG CGG AAG CGC ATC GAG GCC ATC CGC GGC CAG ATC CTG
   --- --- --- --- --- --- --- --- --- --- --- --- --- --- --- --- --- ---
   Asp Met Glu Leu Val Lys Arg Lys Arg Ile Glu Ala Ile Arg Gly Gln Ile Leu 171         180         189         198         207         216
   TCC AAG CTG CGG CTC GCC AGC CCC CCG AGC CAG GGG GAG GTG CCG CCC GGC CCG
   --- --- --- --- --- --- --- --- --- --- --- --- --- --- --- --- --- ---
   Ser Lys Leu Arg Leu Ala Ser Pro Pro Ser Gln Gly Glu Val Pro Pro Gly Pro 225         234         243         252         261         270
   CTG CCC GAG GCC GTG CTC GCC CTG TAC AAC AGC ACC CGC GAC CGG GTG GCC GGG
   --- --- --- --- --- --- --- --- --- --- --- --- --- --- --- --- --- ---
   Leu Pro Glu Ala Val Leu Ala Leu Tyr Asn Ser Thr Arg Asp Arg Val Ala Gly 279         288         297         306         315         324
   GAG AGT GCA GAA CCG GAG CCC GAG CCT GAG GCC GAC TAC TAC GCC AAG GAG GTC
   --- --- --- --- --- --- --- --- --- --- --- --- --- --- --- --- --- ---
   Glu Ser Ala Glu Pro Glu Pro Glu Pro Glu Ala Asp Tyr Tyr Ala Lys Glu Val 333         342         351         360         369         378
   ACC CGC GTG CTA ATG GTG GAA ACC CAC AAC GAA ATC TAT GAC AAG TTC AAG CAG
   --- --- --- --- --- --- --- --- --- --- --- --- --- --- --- --- --- ---
   Thr Arg Val Leu Met Val Glu Thr His Asn Glu Ile Tyr Asp Lys Phe Lys Gln 387         396         405         414         423         432
   AGT ACA CAC AGC ATA TAT ATG TTC TTC AAC ACA TCA GAG CTC CGA GAA GCG GTA
   --- --- --- --- --- --- --- --- --- --- --- --- --- --- --- --- --- ---
   Ser Thr His Ser Ile Tyr Met Phe Phe Asn Thr Ser Glu Leu Arg Glu Ala Val 441         450         459         468         477         486
   CCT GAA CCC GTG TTG CTC TCC CGG GCA GAG CTG CGT CTG CTG AGG AGG CTC AAG
   --- --- --- --- --- --- --- --- --- --- --- --- --- --- --- --- --- ---
   Pro Glu Pro Val Leu Leu Ser Arg Ala Glu Leu Arg Leu Leu Arg Arg Leu Lys 495         504         513         522         531         540
   TTA AAA GTG GAG CAG CAC GTG GAG CTG TAC CAG AAA TAC AGC AAC AAT TCC TGG
   --- --- --- --- --- --- --- --- --- --- --- --- --- --- --- --- --- ---
   Leu Lys Val Glu Gln His Val Glu Leu Tyr Gln Lys Tyr Ser Asn Asn Ser Trp 549         558         567         576         585         594
   CGA TAC CTC AGC AAC CGG CTG CTG GCA CCC AGC GAC TCG CCA GAG TGG TTA TCT
   --- --- --- --- --- --- --- --- --- --- --- --- --- --- --- --- --- ---
   Arg Tyr Leu Ser Asn Arg Leu Leu Ala Pro Ser Asp Ser Pro Glu Trp Leu Ser 603         612         621         630         639         648
   TTT GAT GTC ACC GGA GTT GTG CGG CAG TGG TTG AGC CGT GGA GGG GAA ATT GAG
   --- --- --- --- --- --- --- --- --- --- --- --- --- --- --- --- --- ---
   Phe Asp Val Thr Gly Val Val Arg Gln Trp Leu Ser Arg Gly Gly Glu Ile Glu 657         666         675         684         693         702
   GGC TTT CGC CTT AGC GCC CAC TGC TCC TGT GAC AGC AGG GAT AAC ACA CTG CAA
   --- --- --- --- --- --- --- --- --- --- --- --- --- --- --- --- --- ---
   Gly Phe Arg Leu Ser Ala His Cys Ser Cys Asp Ser Arg Asp Asn Thr Leu Gln
```

```
      711           720           729           738           747           756
GTG GAC ATC AAC GGG TTC ACT ACC GGC CGC CGA GGT GAC CTG GCC ACC ATT CAT
--- --- --- --- --- --- --- --- --- --- --- --- --- --- --- --- --- ---
Val Asp Ile Asn Gly Phe Thr Thr Gly Arg Arg Gly Asp Leu Ala Thr Ile His 765           774           783           792           801           810
GGC ATG AAC CGG CCT TTC CTG CTT CTC ATG GCC ACC CCG CTG GAG AGG GCC CAG
--- --- --- --- --- --- --- --- --- --- --- --- --- --- --- --- --- ---
Gly Met Asn Arg Pro Phe Leu Leu Leu Met Ala Thr Pro Leu Glu Arg Ala Gln 819           828           837           846           855           864
CAT CTG CAA AGC GAA TTC GGA GGC GGG GGT TCA GAC GTC CAA GAA TTC CGC GGC
--- --- --- --- --- --- --- --- --- --- --- --- --- --- --- --- --- ---
His Leu Gln Ser Glu Phe *Gly Gly Gly Gly Ser* Asp Val Gln Glu Phe Arg Gly

873           882           891           900           909           918
GTC ACA GCT GTG ATC CGT GGA GGC GGG GGT TCA GCG GCC GCA CAT ATC CAC GGA
--- --- --- --- --- --- --- --- --- --- --- --- --- --- --- --- --- ---
Val Thr Ala Val Ile Arg *Gly Gly Gly Gly Ser* Ala Ala Ala His Ile His Gly 927           936           945           954           963           972
TGC GAC AAA AAT CAC TTG AGA GAG ATC ATC GGC ATT TTG AAC GAG GTC ACA GGA
--- --- --- --- --- --- --- --- --- --- --- --- --- --- --- --- --- ---
Cys Asp Lys Asn His Leu Arg Glu Ile Ile Gly Ile Leu Asn Glu Val Thr Gly 981           990           999          1008          1017          1026
GAA GGG ACG CCA TGC ACG GAG ATG GAT GTG CCA AAC GTC CTC ACA GCA ACG AAG
--- --- --- --- --- --- --- --- --- --- --- --- --- --- --- --- --- ---
Glu Gly Thr Pro Cys Thr Glu Met Asp Val Pro Asn Val Leu Thr Ala Thr Lys 1035          1044          1053          1062          1071          1080
AAC ACC ACA GAG AGT GAG CTC GTC TGT AGG GCT TCC AAG GTG CTT CGC ATA TTT
--- --- --- --- --- --- --- --- --- --- --- --- --- --- --- --- --- ---
Asn Thr Thr Glu Ser Glu Leu Val Cys Arg Ala Ser Lys Val Leu Arg Ile Phe 1089          1098          1107          1116          1125          1134
TAT TTA AAA CAT GGG AAA ACT CCA TGC TTG AAG AAG AAC TCT AGT GTT CTC ATG
--- --- --- --- --- --- --- --- --- --- --- --- --- --- --- --- --- ---
Tyr Leu Lys His Gly Lys Thr Pro Cys Leu Lys Lys Asn Ser Ser Val Leu Met 1143          1152          1161          1170          1179          1188
GAG CTG CAG AGA CTC TTT CGG GCT TTT CGA TGC CTG GAT TCA TCG ATA AGC TGC
--- --- --- --- --- --- --- --- --- --- --- --- --- --- --- --- --- ---
Glu Leu Gln Arg Leu Phe Arg Ala Phe Arg Cys Leu Asp Ser Ser Ile Ser Cys 1197          1206          1215          1224          1233          1242
ACC ATG AAT GAG TCC AAG TCC ACA TCA CTG AAA GAC TTT CTG GAA AGC CTA AAG
--- --- --- --- --- --- --- --- --- --- --- --- --- --- --- --- --- ---
Thr Met Asn Glu Ser Lys Ser Thr Ser Leu Lys Asp Phe Leu Glu Ser Leu Lys 1251          1260          1269          1278          1287          1296
AGC ATC ATG CAA ATG GAT TAC TCG CAC CAT CAC CAC CAC CCA TTG AGG GCC CTA
--- --- --- --- --- --- --- --- --- --- --- --- --- --- --- --- --- ---
Ser Ile Met Gln Met Asp Tyr Ser His His His His His Pro Leu Arg Ala Leu 1305          1314          1323          1332          1341          1350
TTC TAT AGT GTC ACC TAA ATG CTA GAG CTC GCT GAT CAG CCT CGA CTG TGC CTT
--- --- --- --- --- --- --- --- --- --- --- --- --- --- --- --- --- ---
Phe Tyr Ser Val Thr *** Met Leu Glu Leu Ala Asp Gln Pro Arg Leu Cys Leu

1359
CTA GTT GCC AGC C 3'
--- --- --- --- -
Leu Val Ala Ser
```

FIG. 4 CONT'D

FIG. 5

```
             9              18              27              36              45              54
5' ATG CCG CCC TCC GGG CTG CGG CTG CTG CCG CTG CTG CTA CCG CTG CTG TGG CTA
   Met Pro Pro Ser Gly Leu Arg Leu Leu Pro Leu Leu Leu Pro Leu Leu Trp Leu 63              72              81              90              99             108
   CTG GTG CTG ACG CCT GGC CCG CCG GCC GCG GGA CTA TCC ACC TGC AAG ACT ATC
   Leu Val Leu Thr Pro Gly Pro Pro Ala Ala Gly Leu Ser Thr Cys Lys Thr Ile 117             126             135             144             153             162
   GAC ATG GAG CTG GTG AAG CGG AAG CGC ATC GAG GCC ATC CGC GGC CAG ATC CTG
   Asp Met Glu Leu Val Lys Arg Lys Arg Ile Glu Ala Ile Arg Gly Gln Ile Leu 171             180             189             198             207             216
   TCC AAG CTG CGG CTC GCC AGC CCC CCG AGC CAG GGG GAG GTG CCG CCC GGC CCG
   Ser Lys Leu Arg Leu Ala Ser Pro Pro Ser Gln Gly Glu Val Pro Pro Gly Pro 225             234             243             252             261             270
   CTG CCC GAG GCC GTG CTC GCC CTG TAC AAC AGC ACC CGC GAC CGG GTG GCC GGG
   Leu Pro Glu Ala Val Leu Ala Leu Tyr Asn Ser Thr Arg Asp Arg Val Ala Gly 279             288             297             306             315             324
   GAG AGT GCA GAA CCG GAG CCC GAG CCT GAG GCC GAC TAC TAC GCC AAG GAG GTC
   Glu Ser Ala Glu Pro Glu Pro Glu Pro Glu Ala Asp Tyr Tyr Ala Lys Glu Val 333             342             351             360             369             378
   ACC CGC GTG CTA ATG GTG GAA ACC CAC AAC GAA ATC TAT GAC AAG TTC AAG CAG
   Thr Arg Val Leu Met Val Glu Thr His Asn Glu Ile Tyr Asp Lys Phe Lys Gln 387             396             405             414             423             432
   AGT ACA CAC AGC ATA TAT ATG TTC TTC AAC ACA TCA GAG CTC CGA GAA GCG GTA
   Ser Thr His Ser Ile Tyr Met Phe Phe Asn Thr Ser Glu Leu Arg Glu Ala Val 441             450             459             468             477             486
   CCT GAA CCC GTG TTG CTC TCC CGG GCA GAG CTG CGT CTG CTG AGG AGG CTC AAG
   Pro Glu Pro Val Leu Leu Ser Arg Ala Glu Leu Arg Leu Leu Arg Arg Leu Lys 495             504             513             522             531             540
   TTA AAA GTG GAG CAG CAC GTG GAG CTG TAC CAG AAA TAC AGC AAC AAT TCC TGG
   Leu Lys Val Glu Gln His Val Glu Leu Tyr Gln Lys Tyr Ser Asn Asn Ser Trp 549             558             567             576             585             594
   CGA TAC CTC AGC AAC CGG CTG CTG GCA CCC AGC GAC TCG CCA GAG TGG TTA TCT
   Arg Tyr Leu Ser Asn Arg Leu Leu Ala Pro Ser Asp Ser Pro Glu Trp Leu Ser 603             612             621             630             639             648
   TTT GAT GTC ACC GGA GTT GTG CGG CAG TGG TTG AGC CGT GGA GGG GAA ATT GAG
   Phe Asp Val Thr Gly Val Val Arg Gln Trp Leu Ser Arg Gly Gly Glu Ile Glu 657             666             675             684             693             702
   GGC TTT CGC CTT AGC GCC CAC TGC TCC TGT GAC AGC AGG GAT AAC ACA CTG CAA
   Gly Phe Arg Leu Ser Ala His Cys Ser Cys Asp Ser Arg Asp Asn Thr Leu Gln
```

```
        711            720            729            738            747            756
GTG GAC ATC AAC GGG TTC ACT ACC GGC CGC CGA GGT GAC CTG GCC ACC ATT CAT
--- --- --- --- --- --- --- --- --- --- --- --- --- --- --- --- --- ---
Val Asp Ile Asn Gly Phe Thr Thr Gly Arg Arg Gly Asp Leu Ala Thr Ile His 765            774            783            792            801            810
GGC ATG AAC CGG CCT TTC CTG CTT CTC ATG GCC ACC CCG CTG GAG AGG GCC CAG
--- --- --- --- --- --- --- --- --- --- --- --- --- --- --- --- --- ---
Gly Met Asn Arg Pro Phe Leu Leu Leu Met Ala Thr Pro Leu Glu Arg Ala Gln 819            828            837            846            855            864
CAT CTG CAA AGC GAA TTC GGA GGC GGG GGA TCC CAC AAC GAG TTC CGA CAG CGG
--- --- --- --- --- --- --- --- --- --- --- --- --- --- --- --- --- ---
His Leu Gln Ser Glu Phe Gly Gly Gly Gly Ser His Asn Glu Phe Arg Gln Arg 873            882            891            900            909            918
GAG ACA TAT ATG GTC TTC GGA GGC GGG GGT TCA GCG GCC GCA CAT ATC CAC GGA
--- --- --- --- --- --- --- --- --- --- --- --- --- --- --- --- --- ---
Glu Thr Tyr Met Val Phe Gly Gly Gly Gly Ser Ala Ala Ala His Ile His Gly 927            936            945            954            963            972
TGC GAC AAA AAT CAC TTG AGA GAG ATC ATC GGC ATT TTG AAC GAG GTC ACA GGA
--- --- --- --- --- --- --- --- --- --- --- --- --- --- --- --- --- ---
Cys Asp Lys Asn His Leu Arg Glu Ile Ile Gly Ile Leu Asn Glu Val Thr Gly 981            990            999           1008           1017           1026
GAA GGG ACG CCA TGC ACG GAG ATG GAT GTG CCA AAC GTC CTC ACA GCA ACG AAG
--- --- --- --- --- --- --- --- --- --- --- --- --- --- --- --- --- ---
Glu Gly Thr Pro Cys Thr Glu Met Asp Val Pro Asn Val Leu Thr Ala Thr Lys 1035           1044           1053           1062           1071           1080
AAC ACC ACA GAG AGT GAG CTC GTC TGT AGG GCT TCC AAG GTG CTT CGC ATA TTT
--- --- --- --- --- --- --- --- --- --- --- --- --- --- --- --- --- ---
Asn Thr Thr Glu Ser Glu Leu Val Cys Arg Ala Ser Lys Val Leu Arg Ile Phe 1089           1098           1107           1116           1125           1134
TAT TTA AAA CAT GGG AAA ACT CCA TGC TTG AAG AAG AAC TCT AGT GTT CTC ATG
--- --- --- --- --- --- --- --- --- --- --- --- --- --- --- --- --- ---
Tyr Leu Lys His Gly Lys Thr Pro Cys Leu Lys Lys Asn Ser Ser Val Leu Met 1143           1152           1161           1170           1179           1188
GAG CTG CAG AGA CTC TTT CGG GCT TTT CGA TGC CTG GAT TCA TCG ATA AGC TGC
--- --- --- --- --- --- --- --- --- --- --- --- --- --- --- --- --- ---
Glu Leu Gln Arg Leu Phe Arg Ala Phe Arg Cys Leu Asp Ser Ser Ile Ser Cys 1197           1206           1215           1224           1233           1242
ACC ATG AAT GAG TCC AAG TCC ACA TCA CTG AAA GAC TTT CTG GAA AGC CTA AAG
--- --- --- --- --- --- --- --- --- --- --- --- --- --- --- --- --- ---
Thr Met Asn Glu Ser Lys Ser Thr Ser Leu Lys Asp Phe Leu Glu Ser Leu Lys 1251           1260           1269           1278           1287           1296
AGC ATC ATG CAA ATG GAT TAC TCG CAC CAT CAC CAC CAC CCA TTG AGG GCC CTA
--- --- --- --- --- --- --- --- --- --- --- --- --- --- --- --- --- ---
Ser Ile Met Gln Met Asp Tyr Ser His His His His His Pro Leu Arg Ala Leu 1305           1314
TTC TAT AGT GTC ACC TAA 3'
--- --- --- --- --- ---
Phe Tyr Ser Val Thr ***
```

FIG. 5 CONT'D

SEQUENCE LISTING

<160> NUMBER OF SEQ ID NOS: 67

<210> SEQ ID NO 1
<211> LENGTH: 390
<212> TYPE: PRT
<213> ORGANISM: Homo sapiens

<400> SEQUENCE: 1

```
Met Pro Pro Ser Gly Leu Arg Leu Leu Pro Leu Leu Leu Pro Leu Leu
1               5                   10                  15

Trp Leu Leu Val Leu Thr Pro Gly Pro Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Ile Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Gly Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Trp Arg Pro
                245                 250                 255

Phe Leu Leu Leu Met Ala Thr Pro Leu Glu Arg Ala Gln Lys Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365
```

```
Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 2
<211> LENGTH: 414
<212> TYPE: PRT
<213> ORGANISM: Homo sapiens

<400> SEQUENCE: 2

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
    130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Ile Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Trp Leu Gly Phe Lys Ile Ser Leu
210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
        275                 280                 285

Tyr Arg Leu Glu Ser Gln Gln Thr Asn Arg Arg Lys Lys Arg Ala Leu
    290                 295                 300

Asp Ala Ala Tyr Cys Phe Arg Asn Val Gln Asp Asn Cys Cys Leu Arg
305                 310                 315                 320

Pro Leu Tyr Ile Asp Phe Lys Arg Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350
```

```
Leu Trp Ser Ser Asp Thr Gln His Ser Arg Val Leu Ser Leu Tyr Asn
            355                 360                 365

Thr Ile Asn Pro Glu Ala Ser Ala Ser Pro Cys Cys Val Ser Gln Asp
370                 375                 380

Leu Glu Pro Leu Thr Ile Leu Tyr Tyr Ile Gly Lys Ile Pro Lys Ile
385                 390                 395                 400

Glu Gln Leu Ser Asn Met Ile Val Lys Ser Cys Lys Cys Ser
            405                 410

<210> SEQ ID NO 3
<211> LENGTH: 412
<212> TYPE: PRT
<213> ORGANISM: Homo sapiens

<400> SEQUENCE: 3

Met Lys Met His Leu Gln Arg Ala Leu Val Val Leu Ala Leu Leu His
1               5                   10                  15

Phe Ala Thr Val Ser Leu Ser Leu Ser Thr Cys Thr Thr Leu Asp Phe
                20                  25                  30

Gly His Ile Lys Lys Lys Arg Val Glu Ala Ile Arg Gly Gln Ile Leu
            35                  40                  45

Ser Lys Leu Arg Leu Thr Ser Pro Pro Glu Pro Thr Val Met Thr His
50                  55                  60

Val Pro Tyr Gln Val Leu Ala Leu Tyr Asn Ser Thr Arg Glu Leu Leu
65                  70                  75                  80

Glu Glu His Gly Glu Arg Lys Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
            115                 120                 125

Ser Lys Val Phe Arg Phe Asn Val Ser Ser Val Glu Lys Asn Arg Thr
130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
            195                 200                 205

Arg Glu Trp Leu Leu Arg Arg Glu Ser Asn Leu Gly Leu Glu Ile Ser
210                 215                 220

Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
                245                 250                 255

Asp Asp His Gly Arg Gly Asp Leu Gly Arg Leu Lys Lys Gln Lys Asp
            260                 265                 270

Asn Asn Asn Pro His Leu Ile Leu Met Met Ile Pro Pro His Arg Leu
            275                 280                 285

Asp Asn Pro Gly Gln Gly Gly Gln Arg Lys Lys Arg Ala Leu Asp Thr
290                 295                 300

Asn Tyr Cys Phe Arg Asn Leu Glu Glu Asn Cys Cys Val Arg Pro Leu
305                 310                 315                 320
```

```
Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
    370                 375                 380

Pro Leu Thr Ile Leu Tyr Tyr Val Gly Arg Ile Pro Lys Val Glu Gln
385                 390                 395                 400

Leu Ser Asn Met Val Val Lys Ser Cys Lys Cys Ser
                405                 410

<210> SEQ ID NO 4
<211> LENGTH: 304
<212> TYPE: PRT
<213> ORGANISM: Gallus gallus

<400> SEQUENCE: 4

Met Asp Pro Met Ser Ile Gly Pro Lys Ser Cys Gly Gly Ser Pro Trp
1               5                   10                  15

Arg Pro Pro Gly Thr Ala Pro Trp Ser Ile Gly Ser Arg Arg Ala Thr
            20                  25                  30

Ala Ser Ser Ser Cys Ser Thr Ser Ser Arg Val Arg Ala Glu Val Gly
        35                  40                  45

Gly Arg Ala Leu Leu His Arg Ala Glu Leu Arg His Leu Arg Gln Lys
    50                  55                  60

Ala Ala Ala Asp Ser Ala Gly Thr Glu Gln Arg Leu Glu Leu Tyr Gln
65                  70                  75                  80

Gly Tyr Gly Asn Ala Ser Trp Arg Tyr Leu His Gly Arg Ser Val Arg
                85                  90                  95

Ala Thr Ala Asp Asp Glu Trp Leu Ser Phe Asp Val Thr Asp Ala Val
            100                 105                 110

His Gln Trp Leu Ser Gly Ser Glu Leu Ile Gly Val Phe Lys Leu Ser
        115                 120                 125

Val His Cys Pro Cys Glu Met Gly Pro Gly His Ala Asp Glu Met Arg
    130                 135                 140

Ile Ser Ile Glu Gly Phe Glu Gln Gln Arg Gly Asp Met Gln Ser Ile
145                 150                 155                 160

Ala Lys Lys His Arg Arg Val Pro Tyr Val Leu Ala Met Ala Leu Pro
                165                 170                 175

Ala Glu Arg Ala Asn Glu Leu His Ser Ala Arg Arg Arg Arg Asp Leu
            180                 185                 190

Asp Thr Asp Tyr Cys Phe Gly Pro Gly Thr Asp Glu Lys Asn Cys Cys
        195                 200                 205

Val Arg Pro Leu Tyr Ile Asp Phe Arg Lys Asp Leu Gln Trp Lys Trp
    210                 215                 220

Ile His Glu Pro Lys Gly Tyr Met Ala Asn Phe Cys Met Gly Pro Cys
225                 230                 235                 240

Pro Tyr Ile Trp Ser Ala Asp Thr Gln Tyr Ile Lys Val Leu Ala Leu
                245                 250                 255

Tyr Asn Gln His Asn Pro Gly Ala Ser Ala Ala Pro Cys Cys Val Pro
            260                 265                 270

Gln Ile Leu Asp Pro Leu Pro Ile Ile Tyr Tyr Val Gly Arg Asn Val
        275                 280                 285
```

Arg Val Glu Gln Leu Ser Asn Met Val Val Arg Ala Cys Lys Cys Ser
    290                 295                 300

<210> SEQ ID NO 5
<211> LENGTH: 383
<212> TYPE: PRT
<213> ORGANISM: Xenopus laevis

<400> SEQUENCE: 5

Met Glu Val Leu Trp Met Leu Leu Val Leu Leu Val Leu His Leu Ser
1               5                   10                  15

Ser Leu Ala Asn Ser Leu Ser Thr Cys Lys Ala Val Asp Met Glu Glu
            20                  25                  30

Val Arg Lys Arg Arg Ile Glu Ala Ile Arg Gly Gln Ile Leu Ser Lys
        35                  40                  45

Leu Lys Leu Asp Lys Ile Pro Asp Val Asp Ser Glu Lys Met Thr Val
    50                  55                  60

Pro Ser Glu Ala Ile Phe Leu Tyr Asn Ser Thr Leu Glu Val Ile Arg
65                  70                  75                  80

Glu Lys Ala Thr Arg Glu Glu Glu His Val Gly His Asp Gln Asn
                85                  90                  95

Ile Gln Asp Tyr Tyr Ala Lys Gln Val Tyr Arg Phe Glu Ser Ile Thr
            100                 105                 110

Glu Leu Glu Asp His Glu Phe Lys Phe Lys Phe Asn Ala Ser His Val
        115                 120                 125

Arg Glu Asn Val Gly Met Asn Ser Leu Leu His Ala Glu Leu Arg
    130                 135                 140

Met Tyr Lys Lys Gln Thr Asp Lys Asn Met Asp Gln Arg Met Glu Leu
145                 150                 155                 160

Phe Trp Lys Tyr Gln Glu Asn Gly Thr Thr His Ser Arg Tyr Leu Glu
                165                 170                 175

Ser Lys Tyr Ile Thr Pro Val Thr Asp Gln Glu Trp Asn Ser Phe Asp
            180                 185                 190

Val Thr Lys Thr Val Asn Glu Trp Leu Lys Arg Ala Glu Glu Asn Glu
        195                 200                 205

Gln Phe Gly Leu Gln Pro Ala Gly Lys Gly Pro Thr Pro Gln Ala Lys
    210                 215                 220

Asp Ile Asp Ile Glu Gly Phe Pro Ala Leu Arg Gly Asp Leu Ala Ser
225                 230                 235                 240

Leu Ser Ser Lys Glu Asn Thr Lys Pro Tyr Leu Met Ile Thr Ser Met
                245                 250                 255

Pro Ala Glu Arg Ile Asp Thr Val Thr Ser Ser Arg Lys Lys Arg Gly
            260                 265                 270

Val Gly Gln Glu Tyr Cys Phe Gly Asn Asn Gly Pro Asn Cys Cys Val
        275                 280                 285

Lys Pro Leu Tyr Ile Asn Phe Arg Lys Asp Leu Gly Trp Lys Trp Ile
    290                 295                 300

His Glu Pro Lys Gly Tyr Glu Ala Asn Tyr Cys Leu Gly Asn Cys Pro
305                 310                 315                 320

Tyr Ile Trp Ser Met Asp Thr Gln Tyr Ser Lys Val Leu Ser Leu Tyr
                325                 330                 335

Asn Gln His Asn Pro Gly Ala Ser Ile Ser Pro Cys Cys Val Pro Asp
            340                 345                 350

Val Leu Glu Pro Leu Pro Ile Ile Tyr Tyr Val Gly Arg Ile Ala Lys
        355                 360                 365

```
Val Glu Gln Leu Ser Asn Met Val Val Arg Ser Cys Asn Cys Ser
    370                 375                 380
```

```
<210> SEQ ID NO 6
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 6

Met Met Phe Lys Gly Gln Arg Val Glu Arg Val Leu Thr
1               5                   10

<210> SEQ ID NO 7
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 7

His Asn Glu Phe Arg Gln Arg Glu Thr Tyr Met Val Phe
1               5                   10

<210> SEQ ID NO 8
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 8

Asn Trp Gln Glu Phe Gln Ala Lys Arg Ser Val Ala Tyr
1               5                   10

<210> SEQ ID NO 9
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 9

Leu Glu Leu Lys Ser Asn Ser Val Ile Met Arg Trp Pro
1               5                   10

<210> SEQ ID NO 10
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 10

Asp Tyr Met Glu Val Arg Arg Gln Met Ser Met Gln Met
1               5                   10

<210> SEQ ID NO 11
<211> LENGTH: 13
<212> TYPE: PRT
<213> ORGANISM: Artificial sequence
<220> FEATURE:
```

<223> OTHER INFORMATION: Synthetic sequence: Obtained from a phage
      display library

<400> SEQUENCE: 11

Ala Leu Glu Met Arg Ala Ala Asp Val Glu Tyr His Phe
1               5                   10

<210> SEQ ID NO 12
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 12

Val Glu His Leu Met Glu Val Gln Arg Lys Thr Thr Trp
1               5                   10

<210> SEQ ID NO 13
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 13

Gly Val Glu Val Lys Arg Gln Leu Ser Tyr His Tyr Met
1               5                   10

<210> SEQ ID NO 14
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 14

Gln Glu Leu Val Gly Ala Asn Ile Glu Thr Tyr Met Leu
1               5                   10

<210> SEQ ID NO 15
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 15

Gln Gln Met Glu Val Ser Arg Tyr Val Gln Tyr Lys Trp
1               5                   10

<210> SEQ ID NO 16
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 16

Leu Gln Ser Phe Arg Gln Ala Pro Val Asp Ile Trp Trp
1               5                   10

<210> SEQ ID NO 17

```
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 17

Gln Glu Leu Arg Gly Lys Ile Ser Ile Gln Pro Phe Lys
1               5                   10

<210> SEQ ID NO 18
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 18

Gln Gln Glu Tyr Met Ser Gly Gln Tyr Asp Ile Ile Phe
1               5                   10

<210> SEQ ID NO 19
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 19

Ser Met Glu Phe Ala Ala Thr Val Thr Ser Thr Phe Glu
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 20

Glu Gln Gln Leu Lys Gly Arg Gln Thr His Ile Ile Ile
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 21

Met Glu Leu Lys Gly Gln Thr Asp Met Phe Tyr Ile Ile
1               5                   10

<210> SEQ ID NO 22
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 22

Gly Ala Tyr Ala Val Gly Arg Trp Ser Tyr Val Asp Ala
```

<210> SEQ ID NO 23
<211> LENGTH: 13
<212> TYPE: PRT
<213> ORGANISM: Artificial sequence
<220> FEATURE:
<223> OTHER INFORMATION: Synthetic sequence: Obtained from a phage display library

<400> SEQUENCE: 23

Gly Gln Phe Ala Thr Ser Pro Lys Ile Thr Ile His Lys
1               5                   10

<210> SEQ ID NO 24
<211> LENGTH: 13
<212> TYPE: PRT
<213> ORGANISM: Artificial sequence
<220> FEATURE:
<223> OTHER INFORMATION: Synthetic sequence: Obtained from a phage display library

<400> SEQUENCE: 24

Asp Val Gln Glu Phe Arg Gly Val Thr Ala Val Ile Arg
1               5                   10

<210> SEQ ID NO 25
<211> LENGTH: 13
<212> TYPE: PRT
<213> ORGANISM: Artificial sequence
<220> FEATURE:
<223> OTHER INFORMATION: Synthetic sequence: Obtained from a phage display library

<400> SEQUENCE: 25

His Glu Ala Arg Thr Val Ser Thr Thr Tyr Leu Met Leu
1               5                   10

<210> SEQ ID NO 26
<211> LENGTH: 13
<212> TYPE: PRT
<213> ORGANISM: Artificial sequence
<220> FEATURE:
<223> OTHER INFORMATION: Synthetic sequence: Obtained from a phage display library

<400> SEQUENCE: 26

Tyr Met Glu Met Arg Gly Ser Thr Thr Val Phe Phe Asn
1               5                   10

<210> SEQ ID NO 27
<211> LENGTH: 13
<212> TYPE: PRT
<213> ORGANISM: Artificial sequence
<220> FEATURE:
<223> OTHER INFORMATION: Synthetic sequence: Obtained from a phage display library

<400> SEQUENCE: 27

Gln Glu Leu Ile Gly Ser Tyr Ser Val Met Pro Thr Asn
1               5                   10

<210> SEQ ID NO 28
<211> LENGTH: 13
<212> TYPE: PRT
<213> ORGANISM: Artificial sequence
<220> FEATURE:
<223> OTHER INFORMATION: Synthetic sequence: Obtained from a phage display library

```
<400> SEQUENCE: 28

His Tyr Tyr Met Glu Ala Thr Arg Asp Ile Glu Met Val
1               5                   10

<210> SEQ ID NO 29
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 29

Asn Glu Ala His Ser Ser Gly Ile Thr Ile Met Leu Arg
1               5                   10

<210> SEQ ID NO 30
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 30

Asp His Pro Met Glu Phe Arg Ser Lys Ile Thr Met Lys
1               5                   10

<210> SEQ ID NO 31
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 31

Thr Phe Ala Glu Met Lys Gly Thr Val Ser Tyr Ala Leu
1               5                   10

<210> SEQ ID NO 32
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 32

Gly Val His Met Glu Ser Met Arg Arg Tyr Thr Val Ile
1               5                   10

<210> SEQ ID NO 33
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 33

Phe Gln Glu Tyr Thr Gly Thr Tyr Asp Ile Met Asp Pro
1               5                   10

<210> SEQ ID NO 34
<211> LENGTH: 13
<212> TYPE: PRT
```

```
<213> ORGANISM: Artificial sequence
<220> FEATURE:
<223> OTHER INFORMATION: Synthetic sequence: Obtained from a phage
      display library

<400> SEQUENCE: 34

Phe Gln Ala Val Glu Ala Ser Lys Thr Leu His Phe Trp
1               5                   10

<210> SEQ ID NO 35
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 35

Tyr Leu Glu Thr Ser Arg Thr Tyr Thr Thr Val Trp Pro
1               5                   10

<210> SEQ ID NO 36
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 36

Thr Asp Tyr Leu Glu Val Arg Ser Gln Pro Ile Ile Tyr
1               5                   10

<210> SEQ ID NO 37
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 37

Thr Phe Glu Gln Glu Val Arg Ala Pro Asn Ile Ser Trp
1               5                   10

<210> SEQ ID NO 38
<211> LENGTH: 12
<212> TYPE: PRT
<213> ORGANISM: Artificial sequence
<220> FEATURE:
<223> OTHER INFORMATION: Synthetic sequence: Obtained from a phage
      display library

<400> SEQUENCE: 38

Pro Gln Glu Val Gln Gly Ile Ala Val Glu Trp Val
1               5                   10

<210> SEQ ID NO 39
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 39

Ala Glu Ala Lys Ala Ser Thr Leu His Val Tyr Leu Met
1               5                   10
```

```
<210> SEQ ID NO 40
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 40

Asp Tyr Met Glu Val Val Gly Asn Lys Ile Ser Tyr Ile
1               5                   10

<210> SEQ ID NO 41
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 41

Val Ile Met Glu Ala Val Gly Arg Lys Thr Ile Leu Gln
1               5                   10

<210> SEQ ID NO 42
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 42

Phe Gln Ala Glu Ala Ala Arg Ala Val Thr Tyr Ser Ser
1               5                   10

<210> SEQ ID NO 43
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 43

Glu Asp Tyr Val Tyr Val Lys Asp Val Gly Thr Thr Asn
1               5                   10

<210> SEQ ID NO 44
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 44

Gln Glu Tyr Lys Ala His His Ser Tyr Lys Leu Met Ser
1               5                   10

<210> SEQ ID NO 45
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 45
```

```
Tyr Asn Glu Tyr Arg Ala Thr Pro Thr Phe Ala Val Val
1               5                   10

<210> SEQ ID NO 46
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 46

Glu Tyr Phe His Ala Asn Thr Thr Arg Ile Val Gln Ser
1               5                   10

<210> SEQ ID NO 47
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 47

Ala Leu Glu Ala Ser Arg Phe Ile Ser Trp Asp Ile Asn
1               5                   10

<210> SEQ ID NO 48
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 48

Trp Glu Ala Val Ala Ala Pro Ile Met His Thr Trp Val
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic sequence: Obtained from a phage
      display library

<400> SEQUENCE: 49

Phe Gln Glu Leu Lys Ala Ala Glu Thr Phe Trp Met
1               5                   10

<210> SEQ ID NO 50
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 50

Asn Thr Leu Tyr Ala Val Ala Pro Pro Val Ile Tyr Val
1               5                   10

<210> SEQ ID NO 51
<211> LENGTH: 13
<212> TYPE: PRT
<213> ORGANISM: Artificial sequence
<220> FEATURE:
```

<223> OTHER INFORMATION: Synthetic sequence: Obtained from a phage
      display library

<400> SEQUENCE: 51

Phe Gln Pro Tyr Glu Val Gln Arg Ile Thr Thr Val Met
1               5                   10

<210> SEQ ID NO 52
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 52

Lys Pro Met Glu Ser Gly Arg Arg Thr Thr Val Tyr Tyr
1               5                   10

<210> SEQ ID NO 53
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 53

Met Glu Phe Lys Gly Ala Leu Gln Tyr Arg Leu Gln Pro
1               5                   10

<210> SEQ ID NO 54
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 54

Pro Gln Glu Val Lys Gln Ala Arg Lys Trp Ile Ile Glu
1               5                   10

<210> SEQ ID NO 55
<211> LENGTH: 13
<212> TYPE: PRT
<213> ORGANISM: Artificial sequence
<220> FEATURE:
<223> OTHER INFORMATION: Synthetic sequence: Obtained from a phage
      display library

<400> SEQUENCE: 55

Tyr Arg Gln Gln Glu Val Lys Arg His Ile Gln Ile Val
1               5                   10

<210> SEQ ID NO 56
<211> LENGTH: 9
<212> TYPE: PRT
<213> ORGANISM: Artificial sequence
<220> FEATURE:
<223> OTHER INFORMATION: Synthetic sequence: Consensus ADAMTS-4 cleavage
      motif
<220> FEATURE:
<221> NAME/KEY: VARIANT
<222> LOCATION: (2)..(2)
<223> OTHER INFORMATION: Xaa is Ala, Phe, Val, Leu, Met, or Tyr
<220> FEATURE:
<221> NAME/KEY: VARIANT
<222> LOCATION: (3)..(3)
<223> OTHER INFORMATION: May be present or absent. If present, Xaa

```
              indicates no obvious consensus
<220> FEATURE:
<221> NAME/KEY: VARIANT
<222> LOCATION: (4)..(4)
<223> OTHER INFORMATION: Xaa is Arg or Lys
<220> FEATURE:
<221> NAME/KEY: VARIANT
<222> LOCATION: (5)..(7)
<223> OTHER INFORMATION: Any 1 Xaa may be present or absent: represents
      a range of 2-3 amino acids. If present, Xaa indicates no obvious
      consensus
<220> FEATURE:
<221> NAME/KEY: VARIANT
<222> LOCATION: (8)..(8)
<223> OTHER INFORMATION: Xaa is Ser or Thr
<220> FEATURE:
<221> NAME/KEY: VARIANT
<222> LOCATION: (9)..(9)
<223> OTHER INFORMATION: Xaa is Val, Tyr, Ile, Phe, Trp, Met, Leu, or
      Ala

<400> SEQUENCE: 56

Glu Xaa Xaa Xaa Xaa Xaa Xaa Xaa
1               5

<210> SEQ ID NO 57
<211> LENGTH: 5
<212> TYPE: PRT
<213> ORGANISM: Artificial sequence
<220> FEATURE:
<223> OTHER INFORMATION: Synthetic sequence: Linker

<400> SEQUENCE: 57

Gly Gly Gly Gly Ser
1               5

<210> SEQ ID NO 58
<211> LENGTH: 15
<212> TYPE: PRT
<213> ORGANISM: Artificial sequence
<220> FEATURE:
<223> OTHER INFORMATION: Synthetic sequence: Linker

<400> SEQUENCE: 58

Gly Gly Gly Gly Ser Gly Gly Gly Gly Ser Gly Gly Gly Gly Ser
1               5                   10                  15

<210> SEQ ID NO 59
<211> LENGTH: 1363
<212> TYPE: DNA
<213> ORGANISM: Artificial sequence
<220> FEATURE:
<223> OTHER INFORMATION: Synthetic sequence: Aggrecanase construct with
      B06 cleavage site
<220> FEATURE:
<221> NAME/KEY: CDS
<222> LOCATION: (1)..(1362)

<400> SEQUENCE: 59 atg ccg ccc tcc ggg ctg cgg ctg ctg ccg ctg ctg cta ccg ctg ctg      48
Met Pro Pro Ser Gly Leu Arg Leu Leu Pro Leu Leu Leu Pro Leu Leu
1               5                   10                  15 tgg cta ctg gtg ctg acg cct ggc ccg ccg gcc gcg gga cta tcc acc      96
Trp Leu Leu Val Leu Thr Pro Gly Pro Pro Ala Ala Gly Leu Ser Thr
            20                  25                  30 tgc aag act atc gac atg gag ctg gtg aag cgg aag cgc atc gag gcc     144
Cys Lys Thr Ile Asp Met Glu Leu Val Lys Arg Lys Arg Ile Glu Ala
        35                  40                  45 atc cgc ggc cag atc ctg tcc aag ctg cgg ctc gcc agc ccc ccg agc     192
Ile Arg Gly Gln Ile Leu Ser Lys Leu Arg Leu Ala Ser Pro Pro Ser
```

```
                50                  55                  60
cag ggg gag gtg ccg ccc ggc ccg ctg ccc gag gcc gtg ctc gcc ctg       240
Gln Gly Glu Val Pro Pro Gly Pro Leu Pro Glu Ala Val Leu Ala Leu
 65                  70                  75                  80 tac aac agc acc cgc gac cgg gtg gcc ggg gag agt gca gaa ccg gag       288
Tyr Asn Ser Thr Arg Asp Arg Val Ala Gly Glu Ser Ala Glu Pro Glu
                 85                  90                  95 ccc gag cct gag gcc gac tac tac gcc aag gag gtc acc cgc gtg cta       336
Pro Glu Pro Glu Ala Asp Tyr Tyr Ala Lys Glu Val Thr Arg Val Leu
            100                 105                 110 atg gtg gaa acc cac aac gaa atc tat gac aag ttc aag cag agt aca       384
Met Val Glu Thr His Asn Glu Ile Tyr Asp Lys Phe Lys Gln Ser Thr
        115                 120                 125 cac agc ata tat atg ttc ttc aac aca tca gag ctc cga gaa gcg gta       432
His Ser Ile Tyr Met Phe Phe Asn Thr Ser Glu Leu Arg Glu Ala Val
    130                 135                 140 cct gaa ccc gtg ttg ctc tcc cgg gca gag ctg cgt ctg ctg agg agg       480
Pro Glu Pro Val Leu Leu Ser Arg Ala Glu Leu Arg Leu Leu Arg Arg
145                 150                 155                 160 ctc aag tta aaa gtg gag cag cac gtg gag ctg tac cag aaa tac agc       528
Leu Lys Leu Lys Val Glu Gln His Val Glu Leu Tyr Gln Lys Tyr Ser
                165                 170                 175 aac aat tcc tgg cga tac ctc agc aac cgg ctg ctg gca ccc agc gac       576
Asn Asn Ser Trp Arg Tyr Leu Ser Asn Arg Leu Leu Ala Pro Ser Asp
            180                 185                 190 tcg cca gag tgg tta tct ttt gat gtc acc gga gtt gtg cgg cag tgg       624
Ser Pro Glu Trp Leu Ser Phe Asp Val Thr Gly Val Val Arg Gln Trp
        195                 200                 205 ttg agc cgt gga ggg gaa att gag ggc ttt cgc ctt agc gcc cac tgc       672
Leu Ser Arg Gly Gly Glu Ile Glu Gly Phe Arg Leu Ser Ala His Cys
    210                 215                 220 tcc tgt gac agc agg gat aac aca ctg caa gtg gac atc aac ggg ttc       720
Ser Cys Asp Ser Arg Asp Asn Thr Leu Gln Val Asp Ile Asn Gly Phe
225                 230                 235                 240 act acc ggc cgc cga ggt gac ctg gcc acc att cat ggc atg aac cgg       768
Thr Thr Gly Arg Arg Gly Asp Leu Ala Thr Ile His Gly Met Asn Arg
                245                 250                 255 cct ttc ctg ctt ctc atg gcc acc ccg ctg gag agg gcc cag cat ctg       816
Pro Phe Leu Leu Leu Met Ala Thr Pro Leu Glu Arg Ala Gln His Leu
            260                 265                 270 caa agc gaa ttc gga ggc ggg ggt tca gac gtc caa gaa ttc cgc ggc       864
Gln Ser Glu Phe Gly Gly Gly Gly Ser Asp Val Gln Glu Phe Arg Gly
        275                 280                 285 gtc aca gct gtg atc cgt gga ggc ggg ggt tca gcg gcc gca cat atc       912
Val Thr Ala Val Ile Arg Gly Gly Gly Gly Ser Ala Ala Ala His Ile
    290                 295                 300 cac gga tgc gac aaa aat cac ttg aga gag atc atc ggc att ttg aac       960
His Gly Cys Asp Lys Asn His Leu Arg Glu Ile Ile Gly Ile Leu Asn
305                 310                 315                 320 gag gtc aca gga gaa ggg acg cca tgc acg gag atg gat gtg cca aac      1008
Glu Val Thr Gly Glu Gly Thr Pro Cys Thr Glu Met Asp Val Pro Asn
                325                 330                 335 gtc ctc aca gca acg aag aac acc aca gag agt gag ctc gtc tgt agg      1056
Val Leu Thr Ala Thr Lys Asn Thr Thr Glu Ser Glu Leu Val Cys Arg
            340                 345                 350 gct tcc aag gtg ctt cgc ata ttt tat tta aaa cat ggg aaa act cca      1104
Ala Ser Lys Val Leu Arg Ile Phe Tyr Leu Lys His Gly Lys Thr Pro
        355                 360                 365 tgc ttg aag aag aac tct agt gtt ctc atg gag ctg cag aga ctc ttt      1152
Cys Leu Lys Lys Asn Ser Ser Val Leu Met Glu Leu Gln Arg Leu Phe
```

```
                      370                 375                 380
cgg gct ttt cga tgc ctg gat tca tcg ata agc tgc acc atg aat gag   1200
Arg Ala Phe Arg Cys Leu Asp Ser Ser Ile Ser Cys Thr Met Asn Glu
385                 390                 395                 400 tcc aag tcc aca tca ctg aaa gac ttt ctg gaa agc cta aag agc atc   1248
Ser Lys Ser Thr Ser Leu Lys Asp Phe Leu Glu Ser Leu Lys Ser Ile
            405                 410                 415 atg caa atg gat tac tcg cac cat cac cac cac cca ttg agg gcc cta   1296
Met Gln Met Asp Tyr Ser His His His His His Pro Leu Arg Ala Leu
        420                 425                 430 ttc tat agt gtc acc taa atg cta gag ctc gct gat cag cct cga ctg   1344
Phe Tyr Ser Val Thr     Met Leu Glu Leu Ala Asp Gln Pro Arg Leu
    435                     440                 445 tgc ctt cta gtt gcc agc c                                         1363
Cys Leu Leu Val Ala Ser
    450
```

<210> SEQ ID NO 60
<211> LENGTH: 437
<212> TYPE: PRT
<213> ORGANISM: Artificial sequence
<220> FEATURE:
<223> OTHER INFORMATION: Synthetic sequence: Aggrecanase construct
      with B06 cleavage site

<400> SEQUENCE: 60

```
Met Pro Pro Ser Gly Leu Arg Leu Leu Pro Leu Leu Leu Pro Leu Leu
1               5                   10                  15

Trp Leu Leu Val Leu Thr Pro Gly Pro Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65              70                  75                  80

Tyr Asn Ser Thr Arg Asp Arg Val Ala Gly Glu Ser Ala Glu Pro Glu
            85                  90                  95

Pro Glu Pro Glu Ala Asp Tyr Tyr Ala Lys Glu Val Thr Arg Val Leu
        100                 105                 110

Met Val Glu Thr His Asn Glu Ile Tyr Asp Lys Phe Lys Gln Ser Thr
    115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Arg
145                 150                 155                 160

Leu Lys Leu Lys Val Glu Gln His Val Glu Leu Tyr Gln Lys Tyr Ser
                165                 170                 175

Asn Asn Ser Trp Arg Tyr Leu Ser Asn Arg Leu Leu Ala Pro Ser Asp
            180                 185                 190

Ser Pro Glu Trp Leu Ser Phe Asp Val Thr Gly Val Val Arg Gln Trp
        195                 200                 205

Leu Ser Arg Gly Gly Glu Ile Glu Gly Phe Arg Leu Ser Ala His Cys
    210                 215                 220

Ser Cys Asp Ser Arg Asp Asn Thr Leu Gln Val Asp Ile Asn Gly Phe
225                 230                 235                 240

Thr Thr Gly Arg Arg Gly Asp Leu Ala Thr Ile His Gly Met Asn Arg
                245                 250                 255
```

```
Pro Phe Leu Leu Leu Met Ala Thr Pro Leu Glu Arg Ala Gln His Leu
            260                 265                 270

Gln Ser Glu Phe Gly Gly Gly Ser Asp Val Gln Glu Phe Arg Gly
        275                 280                 285

Val Thr Ala Val Ile Arg Gly Gly Gly Ser Ala Ala His Ile
    290                 295                 300

His Gly Cys Asp Lys Asn His Leu Arg Glu Ile Ile Gly Ile Leu Asn
305                 310                 315                 320

Glu Val Thr Gly Glu Gly Thr Pro Cys Thr Glu Met Asp Val Pro Asn
                325                 330                 335

Val Leu Thr Ala Thr Lys Asn Thr Thr Glu Ser Glu Leu Val Cys Arg
            340                 345                 350

Ala Ser Lys Val Leu Arg Ile Phe Tyr Leu Lys His Gly Lys Thr Pro
        355                 360                 365

Cys Leu Lys Lys Asn Ser Ser Val Leu Met Glu Leu Gln Arg Leu Phe
    370                 375                 380

Arg Ala Phe Arg Cys Leu Asp Ser Ser Ile Ser Cys Thr Met Asn Glu
385                 390                 395                 400

Ser Lys Ser Thr Ser Leu Lys Asp Phe Leu Glu Ser Leu Lys Ser Ile
                405                 410                 415

Met Gln Met Asp Tyr Ser His His His His Pro Leu Arg Ala Leu
            420                 425                 430

Phe Tyr Ser Val Thr
            435

<210> SEQ ID NO 61
<211> LENGTH: 16
<212> TYPE: PRT
<213> ORGANISM: Artificial sequence
<220> FEATURE:
<223> OTHER INFORMATION: Synthetic Construct

<400> SEQUENCE: 61

Met Leu Glu Leu Ala Asp Gln Pro Arg Leu Cys Leu Leu Val Ala Ser
1               5                   10                  15

<210> SEQ ID NO 62
<211> LENGTH: 1314
<212> TYPE: DNA
<213> ORGANISM: Artificial sequence
<220> FEATURE:
<223> OTHER INFORMATION: Synthetic sequence: Aggrecanase construct with
      B05 cleavage site
<220> FEATURE:
<221> NAME/KEY: CDS
<222> LOCATION: (1)..(1314)

<400> SEQUENCE: 62 atg ccg ccc tcc ggg ctg cgg ctg ctg ccg ctg ctg cta ccg ctg ctg      48
Met Pro Pro Ser Gly Leu Arg Leu Leu Pro Leu Leu Leu Pro Leu Leu
1               5                   10                  15 tgg cta ctg gtg ctg acg cct ggc ccg ccg gcc gcg gga cta tcc acc      96
Trp Leu Leu Val Leu Thr Pro Gly Pro Pro Ala Ala Gly Leu Ser Thr
            20                  25                  30 tgc aag act atc gac atg gag ctg gtg aag cgg aag cgc atc gag gcc     144
Cys Lys Thr Ile Asp Met Glu Leu Val Lys Arg Lys Arg Ile Glu Ala
        35                  40                  45 atc cgc ggc cag atc ctg tcc aag ctg cgg ctc gcc agc ccc ccg agc     192
Ile Arg Gly Gln Ile Leu Ser Lys Leu Arg Leu Ala Ser Pro Pro Ser
    50                  55                  60
```

```
cag ggg gag gtg ccg ccc ggc ccg ctg ccc gag gcc gtg ctc gcc ctg         240
Gln Gly Glu Val Pro Pro Gly Pro Leu Pro Glu Ala Val Leu Ala Leu
65              70                  75                  80 tac aac agc acc cgc gac cgg gtg gcc ggg gag agt gca gaa ccg gag         288
Tyr Asn Ser Thr Arg Asp Arg Val Ala Gly Glu Ser Ala Glu Pro Glu
            85                  90                  95 ccc gag cct gag gcc gac tac tac gcc aag gag gtc acc cgc gtg cta         336
Pro Glu Pro Glu Ala Asp Tyr Tyr Ala Lys Glu Val Thr Arg Val Leu
            100                 105                 110 atg gtg gaa acc cac aac gaa atc tat gac aag ttc aag cag agt aca         384
Met Val Glu Thr His Asn Glu Ile Tyr Asp Lys Phe Lys Gln Ser Thr
            115                 120                 125 cac agc ata tat atg ttc ttc aac aca tca gag ctc cga gaa gcg gta         432
His Ser Ile Tyr Met Phe Phe Asn Thr Ser Glu Leu Arg Glu Ala Val
130             135                 140 cct gaa ccc gtg ttg ctc tcc cgg gca gag ctg cgt ctg ctg agg agg         480
Pro Glu Pro Val Leu Leu Ser Arg Ala Glu Leu Arg Leu Leu Arg Arg
145             150                 155                 160 ctc aag tta aaa gtg gag cag cac gtg gag ctg tac cag aaa tac agc         528
Leu Lys Leu Lys Val Glu Gln His Val Glu Leu Tyr Gln Lys Tyr Ser
                165                 170                 175 aac aat tcc tgg cga tac ctc agc aac cgg ctg ctg gca ccc agc gac         576
Asn Asn Ser Trp Arg Tyr Leu Ser Asn Arg Leu Leu Ala Pro Ser Asp
            180                 185                 190 tcg cca gag tgg tta tct ttt gat gtc acc gga gtt gtg cgg cag tgg         624
Ser Pro Glu Trp Leu Ser Phe Asp Val Thr Gly Val Val Arg Gln Trp
            195                 200                 205 ttg agc cgt gga ggg gaa att gag ggc ttt cgc ctt agc gcc cac tgc         672
Leu Ser Arg Gly Gly Glu Ile Glu Gly Phe Arg Leu Ser Ala His Cys
210             215                 220 tcc tgt gac agc agg gat aac aca ctg caa gtg gac atc aac ggg ttc         720
Ser Cys Asp Ser Arg Asp Asn Thr Leu Gln Val Asp Ile Asn Gly Phe
225             230                 235                 240 act acc ggc cgc cga ggt gac ctg gcc acc att cat ggc atg aac cgg         768
Thr Thr Gly Arg Arg Gly Asp Leu Ala Thr Ile His Gly Met Asn Arg
                245                 250                 255 cct ttc ctg ctt ctc atg gcc acc ccg ctg gag agg gcc cag cat ctg         816
Pro Phe Leu Leu Leu Met Ala Thr Pro Leu Glu Arg Ala Gln His Leu
            260                 265                 270 caa agc gaa ttc gga ggc ggg gga tcc cac aac gag ttc cga cag cgg         864
Gln Ser Glu Phe Gly Gly Gly Gly Ser His Asn Glu Phe Arg Gln Arg
            275                 280                 285 gag aca tat atg gtc ttc gga ggc ggg ggt tca gcg gcc gca cat atc         912
Glu Thr Tyr Met Val Phe Gly Gly Gly Ser Ala Ala Ala His Ile
            290                 295                 300 cac gga tgc gac aaa aat cac ttg aga gag atc atc ggc att ttg aac         960
His Gly Cys Asp Lys Asn His Leu Arg Glu Ile Ile Gly Ile Leu Asn
305             310                 315                 320 gag gtc aca gga gaa ggg acg cca tgc acg gag atg gat gtg cca aac        1008
Glu Val Thr Gly Glu Gly Thr Pro Cys Thr Glu Met Asp Val Pro Asn
                325                 330                 335 gtc ctc aca gca acg aag aac acc aca gag agt gag ctc gtc tgt agg        1056
Val Leu Thr Ala Thr Lys Asn Thr Thr Glu Ser Glu Leu Val Cys Arg
            340                 345                 350 gct tcc aag gtg ctt cgc ata ttt tat tta aaa cat ggg aaa act cca        1104
Ala Ser Lys Val Leu Arg Ile Phe Tyr Leu Lys His Gly Lys Thr Pro
            355                 360                 365 tgc ttg aag aag aac tct agt gtt ctc atg gag ctg cag aga ctc ttt        1152
Cys Leu Lys Lys Asn Ser Ser Val Leu Met Glu Leu Gln Arg Leu Phe
370             375                 380
```

```
cgg gct ttt cga tgc ctg gat tca tcg ata agc tgc acc atg aat gag   1200
Arg Ala Phe Arg Cys Leu Asp Ser Ser Ile Ser Cys Thr Met Asn Glu
385                 390                 395                 400 tcc aag tcc aca tca ctg aaa gac ttt ctg gaa agc cta aag agc atc   1248
Ser Lys Ser Thr Ser Leu Lys Asp Phe Leu Glu Ser Leu Lys Ser Ile
            405                 410                 415 atg caa atg gat tac tcg cac cat cac cac cac cca ttg agg gcc cta   1296
Met Gln Met Asp Tyr Ser His His His His His Pro Leu Arg Ala Leu
420                 425                 430 ttc tat agt gtc acc taa                                           1314
Phe Tyr Ser Val Thr
        435

<210> SEQ ID NO 63
<211> LENGTH: 437
<212> TYPE: PRT
<213> ORGANISM: Artificial sequence
<220> FEATURE:
<223> OTHER INFORMATION: Synthetic sequence: Aggrecanase construct with
      B05 cleavage site

<400> SEQUENCE: 63

Met Pro Pro Ser Gly Leu Arg Leu Leu Pro Leu Leu Pro Leu Leu
1               5                   10                  15

Trp Leu Val Leu Thr Pro Gly Pro Pro Ala Ala Gly Leu Ser Thr
            20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Arg
145                 150                 155                 160

Leu Lys Leu Lys Val Glu Gln His Val Glu Leu Tyr Gln Lys Tyr Ser
                165                 170                 175

Asn Asn Ser Trp Arg Tyr Leu Ser Asn Arg Leu Leu Ala Pro Ser Asp
            180                 185                 190

Ser Pro Glu Trp Leu Ser Phe Asp Val Thr Gly Val Val Arg Gln Trp
        195                 200                 205

Leu Ser Arg Gly Gly Glu Ile Glu Gly Phe Arg Leu Ser Ala His Cys
210                 215                 220

Ser Cys Asp Ser Arg Asp Asn Thr Leu Gln Val Asp Ile Asn Gly Phe
225                 230                 235                 240

Thr Thr Gly Arg Arg Gly Asp Leu Ala Thr Ile His Gly Met Asn Arg
                245                 250                 255

Pro Phe Leu Leu Leu Met Ala Thr Pro Leu Glu Arg Ala Gln His Leu
            260                 265                 270

Gln Ser Glu Phe Gly Gly Gly Ser His Asn Glu Phe Arg Gln Arg
        275                 280                 285
```

```
Glu Thr Tyr Met Val Phe Gly Gly Gly Ser Ala Ala His Ile
    290                 295                 300
His Gly Cys Asp Lys Asn His Leu Arg Glu Ile Gly Ile Leu Asn
305                 310                 315                 320
Glu Val Thr Gly Glu Gly Thr Pro Cys Thr Glu Met Asp Val Pro Asn
                325                 330                 335
Val Leu Thr Ala Thr Lys Asn Thr Thr Glu Ser Glu Leu Val Cys Arg
            340                 345                 350
Ala Ser Lys Val Leu Arg Ile Phe Tyr Leu Lys His Gly Lys Thr Pro
        355                 360                 365
Cys Leu Lys Lys Asn Ser Ser Val Leu Met Glu Leu Gln Arg Leu Phe
    370                 375                 380
Arg Ala Phe Arg Cys Leu Asp Ser Ser Ile Ser Cys Thr Met Asn Glu
385                 390                 395                 400
Ser Lys Ser Thr Ser Leu Lys Asp Phe Leu Glu Ser Leu Lys Ser Ile
                405                 410                 415
Met Gln Met Asp Tyr Ser His His His His Pro Leu Arg Ala Leu
            420                 425                 430
Phe Tyr Ser Val Thr
        435

<210> SEQ ID NO 64
<211> LENGTH: 76
<212> TYPE: DNA
<213> ORGANISM: Artificial sequence
<220> FEATURE:
<223> OTHER INFORMATION: Synthetic sequence: Oligonucleotide

<400> SEQUENCE: 64
aattcggagg cggggttca gacgtccaag aattccgcgg cgtcacagct gtgatccgtg      60
gaggcggggg ttcagc                                                    76

<210> SEQ ID NO 65
<211> LENGTH: 76
<212> TYPE: DNA
<213> ORGANISM: Artificial sequence
<220> FEATURE:
<223> OTHER INFORMATION: Synthetic sequence: Oligonucleotide

<400> SEQUENCE: 65
ggccgctgaa cccccgcctc cacggatcac agctgtgacg ccgcggaatt cttggacgtc      60 tgaaccccg cctccg                                                      76

<210> SEQ ID NO 66
<211> LENGTH: 76
<212> TYPE: DNA
<213> ORGANISM: Artificial sequence
<220> FEATURE:
<223> OTHER INFORMATION: Synthetic sequence: Oligonucleotide

<400> SEQUENCE: 66
aattcggagg cggggatcc cacaacgagt tccgacagcg ggagacatat atggtcttcg      60
gaggcggggg ttcagc                                                    76

<210> SEQ ID NO 67
<211> LENGTH: 76
```

```
<212> TYPE: DNA
<213> ORGANISM: Artificial sequence
<220> FEATURE:
<223> OTHER INFORMATION: Synthetic sequence: Oligonucleotide

<400> SEQUENCE: 67
ggccgctgaa cccccgcctc cgaagaccat atatgtctcc cgctgtcgga actcgttgtg    60 ggatccccg cctccg                                                    76
```

LATENCY ASSOCIATED PROTEIN CONSTRUCT WITH AGGRECANASE SENSITIVE CLEAVAGE SITE

CROSS-REFERENCE TO RELATED APPLICATIONS

This application is the U.S. National Stage filing of International Application Serial No. PCT/GB2008/004167 filed Dec. 17, 2008, which claims priority to Great Britain Application No. 0724556.6 filed Dec. 17, 2007, each of which is incorporated herein by reference in its entirety.

The present invention relates to the use of proteins, protein derivatives and DNA constructs that confer latency to pharmaceutically active agents where the pharmaceutically agent is released by the action of aggrecanase. Such products are useful in the treatment of arthritis and cancer.

Most cytokines and growth factors are expressed under tight control mechanisms. Their gene expression is regulated by environmental stimuli such as infection, cell-cell interactions, change in extracellular matrix composition and interactions with adhesion molecules or via stimulation with other cytokines.

In addition to the control at the transcriptional and post-transcriptional level, some is cytokines are not released into the medium unless a second signal activates the cell. A third level of regulation for cytokine activity is found in molecules which are secreted in a latent form and become "activated" by releasing the cytokine moiety where processes of inflammation, wound healing and tissue repair takes place (Khalil N, Microbes and Infection, 1, 1255-1263 (1999). In this latter respect, transforming growth factor beta (TGFβ) has received greatest attention.

TGFβ is synthesized as a dimeric latent cytokine composed of an amino terminal latency associated protein (LAP) and the active TGFβ cytokine at its COOH terminal end (Roberts and Sporn, Peptide Growth Factors and their Receptors: Sporn, M B and Roberts, A B, Springer-Verlag, 419-472 (1996); Roth-Eicchorn et al., Hepatology, 28 1588-1596 (1998)). The precursor peptide contains a signal peptide (residues 1-29) necessary for protein secretion and guiding the molecule through the Golgi apparatus to become processed by proteolytic cleavage and glycosylation. The LAP domain is separated from TGFβ by proteolytic cleavage at arginines (277-278). Mature TGFβ begins at alanine 279. The LAP, in addition to protect TGFβ, contains important residues necessary for the interaction with other molecules. Mutations in the LAP domain have recently been associated with the autosomal dominant Camurati-Engelmann disease (Janssens et al., Nature Genetics, 26, 273-275 (2000). Cysteines 224 and 226 are important in the intermolecular disulphide bond between two LAPs. Their mutation to serine renders the molecule "active" (Sanderson et al., Proc. Natl. Acad. Sci. USA, 92, 2572-2576 (1995); Brunner et al., Mol. Endocrinol. 6, 1691-1700 (1992); Brunner et al., J. Biol. Chem., 264, 13660-13664 (1989)). The RGD motif (245-247) facilitates the interaction with integrins (Munger et al., Mol, Biol. of the Cell, 9, 2627-2638 (1998; Derynck R, TIBS, 19, 548-553 (1994)). Nucleic acid encoding TGFβ is described in U.S. Pat. No. 5,801,231.

In most cell types studied, including those of mesenchymal, epithelial and endothelial origin, TGFβ is secreted in a latent form consisting of TGFβ and its latency associated peptide (LAP) propeptide dimers, covalently linked to latent TGFβ-binding proteins (LTBPs). LTBPs are also needed for the secretion and folding of TGFβ (Miyazano et al., EMBO J. 10, 1091-1101 (1991); Miyazano et al., J. Biol. Chem. 267, 5668-5675 (1992); Eklov et al., Cancer Res. 53, 3193-3197 (1993)). Cysteine 33 is important for is the disulphide bridge with the third 8 cysteine-rich repeat of latent TGFβ binding protein (LTBP) (Saharinen et al., The EMBO Journal, 15, 245-253 (1996). Modification of LTBP by enzymes such as thrombospondin (Schultz et al., The Journal of Biological Chemistry, 269, 26783-26788 (1994); Crawford et al., Cell, 93, 1159-1170 (1998)), transglutaminase (Nunes et al., J. Cell, Biol. 136, 1151-1163 (1997); Kojima et al., The Journal of Cell Biology, 121, 439-448 (1993)) and MMP9, MMP2 (Yu and Stamenkovic, Genes and Dev, 14, 163-176 (2000)) could release the active portion of TGFβ from the latent complex.

Cytokines are natural products serving as soluble local mediators of cell-cell interactions. They have a variety of pleiotropic actions, some of which can be harnessed for therapeutic purposes. Targeting of cytokines to specific cell types using scFv (Lode et al., Pharmacol. Ther, 80, 277-292 (1998)) and vWF (Gordon et al., Human Gene Therapy, 8, 1385-1394 (1997)) have focused entirely on the active cytokine moiety of the cytokine complex.

Pharmacologically active proteins or other medicines based on such agents, which have to be administered at very high concentrations systemically in order to achieve biologically effective concentrations in the tissue being targeted, tend to give rise to undesirable systemic effects, for example toxicity, which limit their use and efficacy.

The principles underlying the construction of such a system for providing latency to pharmaceutically active agents using the LAP of TGFβ was described in WO 02/055098. The present inventors have now developed an improved means for providing pharmaceutically active agents in latent form based on this system.

According to a first aspect of the invention there is provided a fusion protein comprising a latency associated peptide (LAP) and a pharmaceutically active agent in which the LAP and the pharmaceutically active agent are connected by an amino acid sequence comprising an aggrecanase proteolytic cleavage site.

The fusion protein comprising a LAP, an aggrecanase proteolytic cleavage site and a pharmaceutically active agent may provide for site specific activation of the latent pharmaceutically active agent. The term "site specific activation" as used herein means, in general terms and not limited to the removal or reduction of latency, conferred on a pharmaceutically active agent, by site-specific cleavage at the aggrecanase proteolytic cleavage site.

Site-specific cleavage at the proteolytic cleavage site is expected to take place concomitantly with the restored activation of the pharmaceutically active agent.

The term "latent pharmaceutically active agent" as used herein may include, but is not limited to, pharmaceutically active agents which are latent due to their association with LAP and an aggrecanase proteolytic cleavage site. Specifically, the pharmaceutically active agent may be latent by virtue of its fusion to a LAP associated aggrecanase proteolytic cleavage site to form a latent fusion protein.

The term "protein" in this text means, in general terms, a plurality of amino acid residues joined together by peptide bonds. It is used interchangeably and means the same as peptide, oligopeptide, oligomer or polypeptide, and includes glycoproteins and derivatives thereof. The term "protein" is also intended to include fragments, analogues and derivatives of a protein wherein the fragment, analogue or derivative retains essentially the same biological activity or function as a reference protein.

The fragment analogue or derivative of the protein as defined in this text, may be at least 6, preferably 10 or 20, or up to 50 or 100 amino acids long.

The fragment, derivative or analogue of the protein may be (i) one in which one or more of the amino acid residues are substituted with a conserved or non-conserved amino acid residue (preferably, a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half life of the polypeptide (for example, polyethylene glycol), or (iv) one in which the additional amino acids are fused to the mature polypeptide, such as a leader or secretory sequence which is employed for purification of the polypeptide. Such fragments, derivatives and analogues are deemed to be within the scope of those skilled in the art from the teachings herein.

Particularly preferred are variants, analogues, derivatives and fragments having the amino acid sequence of the protein in which several e.g. 5 to 10, or 1 to 5, or 1 to 3, 2, 1 or no amino acid residues are substituted, deleted or added in any combination. Especially preferred among these are silent substitutions, additions and deletions, which do not alter the properties and activities of the protein of the present invention. Also especially preferred in this regard are conservative substitutions.

An example of a variant of the present invention is a fusion protein as defined above, apart from the substitution of one or more amino acids with one or more other amino acids. The skilled person is aware that various amino acids have similar properties. One or more such amino acids of a substance can often be substituted by one or more other such amino acids without eliminating a desired activity of that substance.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Amino acid deletions or insertions may also be made relative to the amino acid sequence for the fusion protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced— for example, dosage levels can be reduced.

Amino acid insertions relative to the sequence of the fusion protein above can also be made. This may be done to alter the properties of a substance of the present invention (e.g. to assist in identification, purification or expression, as explained above in relation to fusion proteins).

Amino acid changes relative to the sequence for the fusion protein of the invention can be made using any suitable technique e.g. by using site-directed mutagenesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

A protein according to the invention may have additional N-terminal and/or C-terminal amino acid sequences. Such sequences can be provided for various reasons, for example, glycosylation.

The term "fusion protein" in this text means, in general terms, one or more proteins joined together by chemical means, including hydrogen bonds or salt bridges, or by peptide bonds through protein synthesis or both.

The latency associated peptide (LAP) of the present invention may include, but is not limited to, the coding sequence for the precursor domain of TGFβ or a sequence which is substantially identical thereto.

"Identity" as known in the art is the relationship between two or more polypeptide sequences or two or more polynucleotide sequences, as determined by comparing the sequences. In the art, identity also means the degree of sequence relatedness (homology) between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic acids Research, 12, 387 (1984), BLASTP, BLASTN, and FASTA (Atschul et al., J. Molec. Biol. 215, 403 (1990).

The LAP of the present invention may comprise the precursor domain of TGFβ, for example, the precursor peptide of TGFβ-1, 2 or 3 (from human) (Derynck et al., Nature, 316, 701-705 (1985); De Martin et al., EMBO J. 6 3673-3677 (1987); Hanks et al., Proc. Natl. Acad. Sci. 85, 79-82 (1988); Derynck et al., EMBO J. 7, 3737-3743 (1988); Ten Dyke et al., Proc. Natl. Acad. Sci. USA, 85, 4715-4719 (1988)) TGFβ-4 (from chicken) (Jakowlew et al., Mol. Endocrinol. 2, 1186-1195 (1988)) or TGFβ-5 (from xenopus) (Kondaiah et al., J. Biol. Chem. 265, 1089-1093 (1990)). The term "precursor domain" is defined as a sequence encoding a precursor peptide which does not include the sequence encoding the mature protein. The amino acid sequences of the precursor domain of TGFβ 1 (SEQ ID NO:1), 2 (SEQ ID NO:2), 3 (SEQ ID NO:3), 4 (SEQ ID NO:4) and 5 (SEQ ID NO:5) (Roberts and Sporn, Peptide Growth Factors and their Receptors: Sporn, M B and Roberts, A B, Springer-Verlag, Chapter 8, 422 (1996)) are shown in FIG. 1.

Preferably, the amino acid sequence of the LAP has at least 50% identity, using the default parameters of the BLAST computer program (Atschul et al., J. Mol. Biol. 215, 403-410 (1990) provided by HGMP (Human Genome Mapping Project), at the amino acid level, to the precursor domain of TGFβ 1, 2, 3, 4 or 5 (Roberts and Sporn, Peptide Growth Factors and their Receptors: Sporn, M B and Roberts, A B, Springer-Verlag, Chapter 8, 422 (1996)) as shown in FIG. 1. More preferably, the LAP may have at least 60%, 70%, 80%, 90% and still more preferably 95% (still more preferably at least 99%) identity, at the nucleic acid or amino acid level, to the precursor domain of TGFβ 1, 2, 3, 4 or 5 as shown in FIG. 1 which comprises residues 1 to 278.

The LAP may comprise the LAP of TGFβ 1, 2, 3, 4, or 5 (Roberts and Sporn, Peptide Growth Factors and their Receptors: Sporn, M B and Roberts, A B, Springer-Verlag, Chapter 8, 422 (1996)) as shown in FIG. 1.

The LAP may contain at least two, for example at least 4, 6, 8, 10 or 20 cysteine residues for the formation of disulphide bonds.

The LAP may provide a protective "shell" around the pharmaceutically active agent thereby shielding it and hindering, or preventing, its interaction with other molecules in the cell surface or molecules important for its activity.

The LAP may also comprise a sequence which has at least 50%, 60%, 70%, 80%, 90%, 95% or 99% identity with a LAP sequence of FIG. 1, using the default parameters of the BLAST computer program provided by HGMP, thereto.

The proteolytic cleavage site may comprise any aggrecanase specific cleavage site which is cleavable by an aggrecanase. An aggrecanase cleavage site may comprise a number of amino acid residues recognisable by an aggrecanase. Moreover, the amino acids of the aggrecanase site may be linked by one or more peptide bonds which are cleavable, proteolytically, by aggrecanase.

Aggrecanases which may cleave the aggrecanase site include, but are not limited to ADAMTS-4 (aggrecanase-1), ADAMTS-5 (aggrecanase-2) and ADAMTS-11 (Tortorella, M. D., et al Osteoarthritis Cartilage, 2001. 9(6): p. 539-552); Abbaszade, I., et al J Biol Chem, 1999. 274(33): p. 23443-23450).

The sequences of the protein cleavage sites of ADAMTS-4 (aggrecanase-1) (see SEQ ID NO: 6 to 55, respectively, top to bottom) are shown in FIG. 2. Suitable ADAMTS-4 sites include:

| HNEFRQRETYMVF | (SEQ ID NO: 7) |
| DVQEFRGVTAVIR | (SEQ ID NO: 24) |

The consensus ADAMTS-4 cleavage motif can be represented according to Hills et al (J. Biol. Chem. 282 11101-11109 (2007)) as:

E-[AFVLMY]-X(0,1)-[RK]-X(2,3)-[ST]-[VYIFWMLA] (SEQ ID NO:56)

Preferably, the aggrecanase proteolytic cleavage site of the present invention is cleaved at sites of a disease diagnosed as arthritis or cancer which can be characterized by inflammation and/or tissue remodelling. More preferably, the aggrecanase proteolytic cleavage site of the present invention is cleaved by ADAMTS-4 (aggrecanase-1), ADAMTS-5 (aggrecanase-2) or ADAMTS-11.

The amino acid sequence of the aggrecanase cleavage site may include a sequence which has at least 50%, 60%, 70%, 80%, 90%, 95% or 99% identity, using the default parameters of the BLAST computer program provided by HGMP, thereto. Preferably, the nucleic acid sequence encoding the aggrecanase cleavage site comprises the minimum number of residues required for recognition and cleavage by an aggrecanase.

The present invention may further provide a "linker" peptide. Preferably the linker peptide is linked to the amino acid sequence of the proteolytic cleavage site. The linker peptide may be provided at the C terminal or N terminal end of the amino acid sequence encoding the proteolytic cleavage site. Preferably, the linker peptide is continuous with the amino acid sequence of the proteolytic cleavage site. The linker peptide may comprise the amino acid sequence GGGGS (SEQ ID NO:57) or a multimer thereof (for example a dimer, a trimer, or a tetramer), a suitable linker may be (GGGGS)$_3$ (SEQ ID NO:58), or a sequence of nucleotides which has at least 50%, 60%, 70%, 80%, 90%, 95% or 99% identity, using the default parameters of the BLAST computer program provided by HGMP, thereto.

The term "linker peptide" is intended to define any sequence of amino acid residues which preferably provide a hydrophilic region when contained in an expressed protein. Such a hydrophilic region may facilitate cleavage by an enzyme at the proteolytic cleavage site.

The term "latency" as used herein, may relate to a shielding effect which may hinder interaction between the fusion protein and other molecules in the cell surface. Alternatively the term latency may be used to describe a reduction in the activity (up to and including ablation of activity) of a molecule/agent associated with the fusion protein. The term latency may also relate to a stabilising effect of the fusion protein. The effect may be in full or partial, where a partial effect is sufficient to achieve the latency of the active agent.

The pharmaceutically active agent may be a pharmaceutically active protein which can include, but is not limited to, a growth factor (e.g. TGFβ, epidermal growth factor (EGF), platelet derived growth factor (PDGF), nerve growth factor (NGF), colony stimulating factor (CSF), hepatocyte growth factor, insulin-like growth factor, placenta growth factor); a differentiation factor; a cytokine e.g. an interleukin, (e.g. IL1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 or IL-33 or an interferon (e.g. IFN-α, IFN-β and IFN-γ), tumour necrosis factor (TNF), IFN-γ inducing factor (IGIF), a bone morphogenetic protein (BMP, e.g. BMP-1, BMP-2, BMP-3, BMP-4, BMP-4, BMP-5, BMP-6, BMP-7, BMP-8, BMP-9, BMP10, BMP-11, BMP-12, BMP-13); an interleukin receptor antagonist (e.g. IL-1ra, IL-1RII); a chemokine (e.g. MIPs (Macrophage Inflammatory Proteins) e.g. MIP1α and MIP1β; MCPs (Monocyte Chemotactic Proteins) e.g. MCP1, 2 or 3; RANTES (regulated upon activation normal T-cell expressed and secreted)); a trophic factor; a cytokine inhibitor; a cytokine receptor; a free-radical scavenging enzyme e.g. superoxide dismutase or catalase; a pro-drug converting enzyme (e.g. angiotensin converting enzyme, deaminases, dehydrogenases, reductases, kinases and phosphatases); a peptide mimetic; a protease inhibitor; a tissue inhibitor of metalloproteinases (TIMPs eg. TIMP1, TIMP2, TIMP3 or TIMP4) or a serpin (inhibitors of serine proteases). Preferably, the pharmaceutically active agent will be derived from the species to be treated e.g. human origin for the treatment of humans. Preferably, the pharmaceutically active agent is IFNβ, IL-4, or IL-1ra.

The interleukins and cytokines may be both anti-inflammatory or pro-inflammatory. Anti-inflammatory cytokines and certain interleukins, such as IL-4 and/or IL-10, are suitable for the treatment of arthritis, whereas pro-inflammatory cytokines and other interleukins, such as IL-1 and IL-2, are suitable for the treatment of cancer.

As used herein "peptide mimetics" includes, but is not limited to, agents having a desired peptide backbone conformation embedded into a non-peptide skeleton which holds the peptide in a particular conformation. Peptide mimetics, which do not have some of the drawbacks of peptides, are of interest in those cases where peptides are not suitable in medicine.

Peptide mimetics may comprise a peptide backbone which is of the L- or D-conformation. Examples of peptides mimetics include melanocortin, adrenocorticotrophin hormone (ACTH) and other peptide mimetic agents which play a role in the central nervous system, endocrine system in signal transduction and in infection and immunity.

The pharmaceutically active agent may comprise a chemical compound such as a chemotherapeutic agent or other synthetic drug. Alternatively, the pharmaceutically active agent may comprise an siRNA or a peptide nucleic acid (PNA) sequence e.g. a poly-lysine sequence which binds to nucleic acids and permeabilises lipid bilayers (Wyman et al., Biological Chemistry, 379, 1045-1052 (1998)) or a KALA peptide which facilitates transfer through lipid bilayers (Wyman et al., Biochemistry, 36, 3008-3017 (1997)) or a protein transduction domain (PTD) that enables polypeptides to enter cells via the plasma membrane (Pi et al Molecular Therapy 2, 339-347 (2000)).

The term "associating with" in the context of the present invention is intended to include all means of association including, but not limited to, chemical cross-linking or peptide bond linkage.

In an alternative embodiment, the invention further provides the fusion protein of the present invention optionally in association with latent TGFβ binding protein (LTBP). Typically, the fusion protein is covalently linked to LTBP to form a complex. Preferably, the association is mediated by disulphide bond(s) between Cys No. 33 of LAP and the third 8 Cys residue of LTBP. The LTBP associated with the fusion protein may include, but is not limited to, LTBP 1, 2, 3 or 4 (Kanzaki et al., Cell, 61, 1051-1061 (1990); Tsuji et al., Proc. Natl. Acad. Sci. USA, 87, 8835-8839 (1990); Moren et al., J. Biol. Chem. 269, 32469-32478 (1994); Yin et al., J. Biol. Chem. 270, 10147-10160 (1995); Gibson et al., Mol. Cell. Biol. 15, 6932-6942 (1995); Saharinen et al., J. Biol. Chem. 273, 18459-18469 (1998)), or fragments of LTBP such as that containing the third 8 Cys repeat, or homologues having a sequence of amino acids or nucleotides which has at least 50%, 60%, 70%, 80%, 90%, 95% or 99% identity, using the default parameters of the BLAST computer program provided by HGMP, to that of LTBP.

Cleavage of LTBP may release the fusion protein from the LTBP complex. Enzymes which may cleave LTBP in this manner include, but are not limited to, thrombospondin (Schultz et al., The Journal of Biological Chemistry, 269, 26783-26788 (1994); Crawford et al., Cell, 93, 1159-1170 (1998)), transglutaminase (Nunes et al., J. Cell, Biol. 136, 1151-1163 (1997); Kojima et al., The Journal of Cell Biology, 121, 439-448 (1993)) MMP9 and MMP2 (Yu and Stamenkovic, Genes and Dev, 14, 163-176 (2000)).

The invention further provides nucleic acid encoding the fusion protein of the first aspect of the invention as defined above. A second aspect of the invention provides a nucleic acid construct comprising a first nucleic acid sequence encoding a pharmaceutically active agent, a second nucleic acid sequence encoding a LAP, wherein a nucleic acid sequence encoding an aggrecanase proteolytic cleavage site is provided between the first and second nucleic acid sequences.

The term "nucleic acid construct" generally refers to any length of nucleic acid which may be DNA, cDNA or RNA such as mRNA obtained by cloning or produced by chemical synthesis. The DNA may be single or double stranded. Single stranded DNA may be the coding sense strand, or it may be the non-coding or anti-sense strand. For therapeutic use, the nucleic acid construct is preferably in a form capable of being expressed in the subject to be treated.

Preferably, the first nucleic acid sequence encodes the protein IFNβ, IL-4 or IL-1ra. In one embodiment of the invention, the first nucleic acid sequence encodes IFNβ, IL-4 or IL-1ra from a mouse or a human.

The nucleic acid construct of the second aspect of the invention may be in the form of a vector, for example, an expression vector, and may include, among others, chromosomal, episomal and virus-derived vectors, for example, vectors derived from bacterial plasmids, from bacteriophage, from transposons, from yeast episomes, from insertion elements, from yeast chromosomal elements, from viruses such as baculo-viruses, papova-viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. Generally, any vector suitable to maintain, propagate or express nucleic acid to express a polypeptide in a host, may be used for expression in this regard.

The invention further provides a protein encoded by the nucleic acid construct of the second aspect of the invention optionally in association with latent TGFβ binding protein (LTBP) described herein. Typically, the protein encoded by the nucleic acid construct is covalently linked to LTBP to form a complex. Preferably, the association is mediated by disulphide bond(s) between Cys No. 33 of LAP and the third 8 Cys residue of LTBP.

The nucleic acid construct of the second aspect of the invention preferably includes a promoter or other regulatory sequence which controls expression of the nucleic acid. Promoters and other regulatory sequences which control expression of a nucleic acid have been identified and are known in the art. The person skilled in the art will note that it may not be necessary to utilise the whole promoter or other regulatory sequence. Only the minimum essential regulatory element may be required and, in fact, such elements can be used to construct chimeric sequences or other promoters. The essential requirement is, of course, to retain the tissue and/or temporal specificity. The promoter may be any suitable known promoter, for example, the human cytomegalovirus (CMV) promoter, the CMV immediate early promoter, the HSV thymidinekinase, the early and late SV40 promoters or the promoters of retroviral LTRs, such as those of the Rous Sarcoma virus (RSV) and metallothionine promoters such as the mouse metallothionine-I promoter. The promoter may comprise the minimum comprised for promoter activity (such as a TATA elements without enhancer elements) for example, the minimum sequence of the CMV promoter.

Preferably, the promoter is contiguous to the first and/or second nucleic acid sequence.

As stated herein, the nucleic acid construct of the second aspect of the invention may be in the form of a vector. Vectors frequently include one or more expression markers which enable selection of cells transfected (or transformed) with them, and preferably, to enable a selection of cells containing vectors incorporating heterologous DNA. A suitable start and stop signal will generally be present.

One embodiment of the invention relates to a cell comprising the nucleic acid construct of the second aspect of the invention. The cell may be termed a "host" cell, which is useful for the manipulation of the nucleic acid, including cloning. Alternatively, the cell may be a cell in which to obtain expression of the nucleic acid. Representative examples of appropriate host cells for expression of the nucleic acid construct of the invention include virus packaging cells which allow encapsulation of the nucleic acid into a viral vector; bacterial cells, such as *Streptococci, Staphylococci, E. coli, Streptomyces* and *Bacillus Subtilis*; single cells, such as yeast cells, for example, *Saccharomyces Cerevisiae*, and *Aspergillus* cells; insect cells such as *Drosophila* S2 and *Spodoptera* Sf9 cells, animal cells such as CHO, COS, C127, 3T3, PHK.293, and Bowes Melanoma cells and other suitable human cells; and plant cells e.g. *Arabidopsis thaliana*.

Induction of an expression vector into the host cell can be affected by calcium is phosphate transfection, DEAE-dextran mediated transfection, microinjection, cationic-lipid-mediated transfection, electroporation, transduction, scrape loading, ballistic introduction, infection or other methods. Such methods are described in many standard laboratory manuals, such as Sambrook et al, Molecular Cloning, a Laboratory Manual, Second Edition, Coldspring Harbor Laboratory Press, Coldspring Harbor, N.Y. (1989).

Mature proteins can be expressed in host cells, including mammalian cells such as CHO cells, yeast, bacteria, or other cells under the control of appropriate promoters. Cell-free translation systems can be employed to produce such proteins using RNAs derived from the nucleic acid construct of the third aspect of the present invention. Appropriate cloning and expression vectors for use with prokaryotic and eukaryotic hosts are described by Sambrook et al, Molecular Cloning, a Laboratory Manual, Second Edition, Coldspring Harbor Laboratory Press, Coldspring Harbor, N.Y. (1989).

Proteins can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography, high performance liquid chromatography, lectin and/or heparin chromatography. For therapy, the nucleic acid construct e.g. in the form of a recombinant vector, may be purified by techniques known in the art, such as by means of column chromatography as described in Sambrook et al, Molecular Cloning, a Laboratory Manual, Second Edition, Coldspring Harbor Laboratory Press, Coldspring Harbor, N.Y. (1989).

According to a third aspect of the invention, there is provided a composition in accordance with the first aspect of the invention for use in the treatment of arthritis or cancer. This aspect of the invention therefore extends to and includes a method for the treatment or arthritis or cancer comprising the administration to a subject of a composition comprising a fusion protein comprising a latency associated peptide (LAP) connected by an aggrecanase proteolytic cleavage site to a pharmaceutically active agent.

The present invention provides a composition as described above for use in the treatment of arthritis or cancer. Arthritis defines a group of disease conditions (or arthropathies) where damage is caused to the joints of the body and includes osteoarthritis (also known as degenerative joint disease) which can occur following trauma to the joint, following an infection of the joint or as a result of aging. Other forms of arthritis include rheumatoid arthritis and psoriatic arthritis, which are autoimmune diseases, and septic arthritis is caused by infection in the joints. Cancer defines a group of diseases characterized by an abnormal proliferation of cells in the body, which can be defined as tumors, for example glioblastoma. Glioblastoma is also sometimes referred to as Grade 4 astrocytoma.

In a fourth aspect, the invention provides a nucleic acid sequence in accordance with the second aspect of the invention for use in the treatment of arthritis or cancer. This aspect therefore extends to and includes a method for the treatment of arthritis or cancer comprising the administration to a subject a nucleic acid construct of the second aspect of the invention. Where the nucleic acid construct is used in the therapeutic method of the invention, the construct may be used as part of an expression construct, e.g. in the form of an expression vector such as a plasmid or virus. In such a method, the construct may be administered intravenously, intradermally, intramuscularly, orally or by other routes.

The nucleic acid construct of the second aspect of the invention, and proteins derived therefrom, may be employed alone or in conjunction with other compounds, such as therapeutic compounds, e.g. anti-inflammatory drugs, cytotoxic agents, cytostatic agents or antibiotics. The nucleic acid constructs and proteins useful in the present invention are preferably provided in an isolated form, and preferably are purified to homogeneity.

As used herein, the term "treatment" includes any regime that can benefit a human or a non-human animal. The treatment of "non-human animals" extends to the treatment of domestic animals, including horses and companion animals (e.g. cats and dogs) and farm/agricultural animals including members of the ovine, caprine, porcine, bovine and equine families. The treatment may be in respect of any existing condition or disorder, or may be prophylactic (preventive treatment). The treatment may be of an inherited or an acquired disease. The treatment may be of an acute or chronic condition. Preferably, the treatment is of a condition/disorder associated with inflammation. The first nucleic acid sequence of the nucleic acid construct of the third aspect of the invention may encode a protein for use in the treatment of the disorder, including, but not limited to osteoarthritis, scleroderma, renal disease, rheumatoid arthritis, inflammatory bowel disease, multiple sclerosis, atherosclerosis, cancer, or any inflammatory disease.

The nucleic acid construct of the second aspect of the invention may be used therapeutically in a method of the invention by way of gene therapy. Alternatively, protein encoded by the nucleic acid construct may be directly administered as described herein.

Administration of the nucleic acid construct of the second aspect may be directed to the target site by physical methods. Examples of these include topical administration of the "naked" nucleic acid in the form of a vector in an appropriate vehicle, for example, in solution in a pharmaceutically acceptable excipient, such as phosphate buffered saline, or administration of a vector by physical method such as particle bombardment according to methods known in the art.

Other physical methods for administering the nucleic acid construct or proteins of the third aspect of the invention directly to the recipient include ultrasound, electrical stimulation, electroporation and microseeding. Further methods of administration include oral administration or administration through inhalation.

Particularly preferred is the microseeding mode of delivery which is a system for delivering genetic material into cells in situ in a patient. This method is described in U.S. Pat. No. 5,697,901.

The nucleic acid construct according to the second aspect of the invention may also be administered by means of delivery vectors. These include viral delivery vectors, such as adenovirus, retrovirus or lentivirus delivery vectors known in the art.

Other non-viral delivery vectors include lipid delivery vectors, including liposome delivery vectors known in the art.

Administration may also take place via transformed host cells. Such cells include cells harvested from the subject, into which the nucleic acid construct is transferred by gene transfer methods known in the art. Followed by the growth of the transformed cells in culture and grafting to the subject.

As used herein the term "gene therapy" refers to the introduction of genes by recombinant genetic engineering of body cells (somatic gene therapy) for the benefit of the patient. Furthermore, gene therapy can be divided into ex vivo and in vivo techniques. Ex vivo gene therapy relates to the removal of body cells from a patient, treatment of the removed cells with a vector i.e., a recombinant vector, and subsequent return of the treated cells to the patient. In vivo gene therapy relates to the direct administration of the recombinant gene vector by, for example, intravenous or intravascular means.

Preferably the method of gene therapy of the present invention is carried out ex vivo.

Preferably in gene therapy, the expression vector of the present invention is administered such that it is expressed in the subject to be treated. Thus for human gene therapy, the promoter is preferably a human promoter from a human gene, or from a gene which is typically expressed in humans, such as the promoter from human CMV.

For gene therapy, the present invention may provide a method for manipulating the somatic cells of human and non-human mammals.

The present invention also provides a gene therapy method which may involve the manipulation of the germ line cells of a non-human mammal.

The present invention therefore provides a method for providing a human with a therapeutic protein comprising introducing mammalian cells into a human, the human cells having been treated in vitro to insert therein a nucleic acid construct according to the second aspect of the invention.

Each of the individual steps of the ex vivo somatic gene therapy method are also covered by the present invention. For example, the step of manipulating the cells removed from a patient with the nucleic acid construct of the third aspect of the invention in an appropriate vector. As used herein, the term "manipulated cells" covers cells transfected with a recombinant vector.

Also contemplated is the use of the transfected cells in the manufacture of a medicament for the treatment of arthritis or cancer.

The present invention may also find application in veterinary medicine for treatment/prophylaxis of domestic animals including horses and companion animals (e.g. cats and dogs) and farm animals which may include mammals of the ovine, porcine, caprine, bovine and equine families.

The present invention also relates to compositions comprising the nucleic acid construct or proteins of the first or second aspects of the invention. Therefore, the fusion protein or nucleic acid constructs of the present invention may be employed in combination with the pharmaceutically acceptable carrier or carriers. Such carriers may include, but are not limited to, saline, buffered saline, dextrose, liposomes, water, glycerol, ethanol and combinations thereof.

The pharmaceutical compositions may be administered in any effective, convenient manner effective for treating a patients disease including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

For administration to mammals, and particularly humans, it is expected that the daily dosage of the active agent will be from 0.01 mg/kg body weight, typically around 1 mg/kg. The physician in any event will determine the actual dosage which will be most suitable for an individual which will be dependent on factors including the age, weight, sex and response of the individual. The above dosages are exemplary of the average case. There can, of course, be instances where higher or lower dosages are merited, and such are within the scope of this invention A sixth aspect of the invention provides a fusion protein comprising a LAP and an aggrecanase proteolytic cleavage site wherein the fusion protein is associated with a pharmaceutically active agent. The pharmaceutically active agent may be as described above. In some embodiments of this aspect of the invention, the pharmaceutically active agent may be an siRNA or PNA molecule.

The invention further provides a nucleic acid construct encoding the fusion protein of the sixth aspect of the invention. The nucleic acid construct preferably comprises a nucleic acid sequence encoding a LAP adjacent a nucleic acid sequence encoding an aggrecanase proteolytic cleavage site. Preferably, the nucleic acid sequence encoding a LAP is suitably operably linked to a nucleic acid sequence encoding an aggrecanase proteolytic cleavage site.

The invention further provides the fusion protein of the sixth aspect of the invention optionally in association with latent TGFβ binding protein (LTBP) described herein.

The fusion protein of the sixth aspect of the invention may be associated with the pharmaceutically active agent by means of a peptide bond linkage. Alternatively, the fusion protein may be associated with the pharmaceutically active agent by means of a chemical linkage e.g. by cross-linking the fusion protein to a chemical compound such as a chemotherapeutic agent, synthetic drug or PNA.

Preferably, the pharmaceutically active agent is linked to the C-terminal end of the amino acid sequence of the proteolytic cleavage site in the fusion protein of the seventh aspect of the invention. More preferably, the pharmaceutically active agent is continuous with the C-terminal residue of the amino acid sequence of the aggrecanase proteolytic cleavage site.

The fusion protein, and associated pharmaceutically active agent of the sixth aspect of the invention may be employed alone or in conjunction with other compounds, such as therapeutic compounds, e.g. anti-inflammatory drugs, cytotoxic agents, cytostatic agents or antibiotics. Such administration may be simultaneous, separate or sequential. The components may be prepared in the form of a kit which may comprise instructions as appropriate.

Preferably, the fusion protein and associated pharmaceutically active agent of the sixth aspect of the invention are directly administered to a patient as described herein.

The present invention also relates to compositions comprising the fusion protein and associated pharmaceutically active agent of the sixth aspect of the invention. Therefore, the fusion protein and associated pharmaceutically active agent may be employed in combination with the pharmaceutically acceptable carrier or carriers. Such carriers may include, but are not limited to, saline, buffered saline, dextrose, liposomes, water, glycerol, polyethylene glycol, ethanol and combinations thereof.

The pharmaceutical compositions may be administered in any effective, convenient manner effective for treating a disease of a patient including, for instance, administration by oral, topical, intravenous, intramuscular, intranasal, or intradermal routes among others. In therapy or as a prophylactic, the active agent may be administered to an individual as an injectable composition, for example as a sterile aqueous dispersion, preferably isotonic.

A seventh aspect of the invention provides a kit of parts comprising a fusion protein of the first aspect of the invention, a nucleic acid construct of the second aspect of the invention, or a fusion protein and associated pharmaceutically active agent according to the sixth aspect of the invention, and an administration vehicle including, but not limited to, tablets for oral administration, inhalers for lung administration and injectable solutions for intravenous administration.

An eighth aspect of the invention provides a process for preparing the fusion protein, of the first aspect of the invention comprising production of the fusion protein recombinantly by expression in a host cell, purification of the expressed fusion protein and association of the pharmaceutically active agent to the purified fusion protein by means of peptide bond linkage, hydrogen or salt bond or chemical cross linking. In some embodiments of this aspect of the invention where the pharmaceutically active agent is a peptide, the fusion protein could be prepared using hydrogen or salt bonds where the peptide is capable or multimerisation, for example dimerisation or trimerisation.

A ninth aspect of the invention provides a process for preparing a nucleic acid construct of the second aspect of the invention comprising ligating together nucleic acid sequences encoding a latency associated peptide, an aggrecanase cleavage sequence, and a pharmaceutically active agent, optionally including a linker sequence on either side of the aggrecanase cleavage site.

A preferred embodiment of the present invention provides a method of providing latency to a pharmaceutically active agent which is a cytokine, preferably interferon or an interleukin, the method comprising constructing a fusion protein having a latency associated peptide, preferably from TGFβ, associated with an aggrecanase proteolytic cleavage site, preferably an ADAM-TS4 cleavage site, and the pharmaceutically active agent. Preferably, the pharmaceutically active agent is followed by the proteolytic cleavage site and the LAP as follows: LAP-cleavage site-active agent.

All preferred features of the second and subsequent aspects of the invention are as for the first aspect mutatis mutandis.

The present invention will now be described by way of example only with reference to the accompanying figures wherein:

FIG. 1 shows amino acid sequences of the precursor domain of TGFβ 1, 2 and 3 (human, Hu), TGFβ 4 (chicken, Ck), TGFβ (frog, Fg). Arrows indicate the position of the proteolytic processing resulting in cleavage of the signal peptide of TGFβ1 and of the mature TGFβs. N-linked glycosylation sites are underlined, as is the integrin cellular recognition sequence (Roberts and Sporn, Peptide Growth Factors and their Receptors: Sporn, M B and Roberts, A B, Springer-Verlag, Chapter 8, 422 (1996)); (SEQ ID NO:1, SEQ ID NO:2, SEQ ID NO:3, SEQ ID NO:4, and SEQ ID NO:5, respectively).

FIG. 2 shows a multiple sequence alignment of the ADAMTS-4 epitope sequences with corresponding average percentage of phagemid cleavage and the derived ADAMTS-4 cleavage motif. Predominant amino acids found at a frequency of greater than 40% in a particular position are illustrated with a black background, in contrast to related amino acids which are shown with a grey background (reproduced from Hills et al J. Biol. Chem. 282 11101-11109 (2007)). (SEQ ID NO:6 to SEQ ID NO:55, top to bottom).

FIG. 3 shows the development of ADAMTS-4 sensitive LAP-IL-4. Western blot of supernatants of transiently transfected 293T cells probed with anti-IL-4 antibody. Serum free supernatants were collected 48 hrs after transfection and incubated overnight at 37 C without (−) or with (+) recombinant MMP-1 or aggrecanase (both kindly provided by H. Nagase, Kennedy Institute). Note specificity of cleavage LAP-MMP IL-4 is only cleaved by MMP-1 whilst the Agg1 and Agg2 constructs are cleaved by ADAMTS-4 but not MMP-1. Agg1 and Agg2 correspond to the sequences B05 and B06 from Hills et al. (J. Biol. Chem. 282(15):11101-11109; (2007)).

FIGS. 4 and 5 show the full open reading frame and DNA sequence of both aggrecanase constructs. The GGGS sequences before and after the aggrecanase site are italicized, the EcoR1 and Not1 cloning sites are bold and underlined. The aggrecanase sites are in bold. The mIL-4 has a poly Histidine tail and tagged epitope at the COOH end. FIG. 4 shows the construct with the B06 cleavage site (SEQ ID NO:59 and SEQ ID NO:60) and FIG. 5 shows the construct with the B05 cleavage site (SEQ ID NO:62 and SEQ ID NO:63).

The invention is now described with reference to the following non-limiting examples;

Experiment 1

Development of ADAMTS-4 Sensitive LAP-IL-4

The aggrecanase cleavage sites B05 and B06 reported by Hills et al (J. Biol. Chem. 282: 11101-11109 (2007)) were flanked on either side with the linker $(GGGGS)_3$ (SEQ ID NO:58) using overlapping oligodeoxynucleotides that were cloned between the EcoR1 and Not1 sites of the LAP-IL-4 construct (see FIG. 4 or FIG. 5).

To clone the aggrecanase cleavage sites into LAP-mIL-4, the following oligonucleotides coding for the cleavage sites B05 and B06 were purified by HPLC for cloning.

```
B06: DVQEFRGVTAVIR with GGGGS at either end
                                        (SEQ ID NO:
 64)
                                          Aat II
1. sense (B06)5' aattc GGA GGC GGG GGT TCA GAC GTC
CAA GAA TTC CGC GGC GTC ACA GCT GTG ATC CGT GGA
GGC GGG GGT TCA gc (SEQ ID NO: 65)
2. antisense (B06)5' ggc cgc TGA ACC CCC GCC TCC
ACG GAT CAC AGC TGT GAC GCC GCG GAA TTC TTG GAC GTC
TGA ACC CCC GCC TCC g B05: HNEFRQRETYMVF with GGGGS at either end
                                       (SEQ ID NO: 66)
                                 BamH1
3. sense(B05) 5' aattc GGA GGC GGG GGA TCC CAC AAC
GAG TTC CGA CAG CGG GAG ACA TAT ATG GTC TTC GGA
GGC GGG GGT TCA gc (SEQ ID NO: 67)
4. antisense (B05) 5' ggc cgc TGA ACC CCC GCC TCC
GAA GAC CAT ATA TGT CTC CCG CTG TCG GAA CTC GTT
GTG GGA TCC CCC GCC TCC g
```

To prepare the final construct, the LAP-mIL4 construct was cut with EcoR1 and Not1 and the large fragment produced was purified. After annealing the oligonucleotides the cleavage sequences were cloned into them. Positive clones were sent for DNA sequencing. B05 has new Aat II site, and B06 has a BamH1 site.

The invention claimed is:

1. A fusion protein comprising a latency associated peptide (LAP) which is the precursor domain of TGFβ-1, -2, -3, -4 or -5 and a cytokine in which the LAP and cytokine are connected by an amino acid sequence comprising an aggrecanase proteolytic cleavage site which is DVQEFRGVTAVIR (SEQ ID NO:24).

2. A fusion protein as claimed in claim 1, in which a peptide linker sequence is present adjacent to the aggrecanase cleavage site.

3. A fusion protein as claimed in claim 2, in which the peptide linker sequence is GGGGS (SEQ ID NO:57), or a multimer thereof.

4. A pharmaceutical composition comprising a fusion protein as claimed in claim 1.

5. A nucleic acid construct comprising a first nucleic acid sequence encoding a cytokine, a second nucleic acid sequence encoding a LAP which is the latency associated peptide (LAP) of TGFβ-1, -2, -3, -4 or -5, and a nucleic acid sequence encoding an aggrecanase proteolytic cleavage site which is DVQEFRGVTAVIR (SEQ ID NO: 24) and wherein said site is provided between the first and second nucleic acid sequences.

6. A vector comprising a nucleic acid construct as claimed in claim 5.

7. A fusion protein encoded by a nucleic acid construct comprising a first nucleic acid sequence encoding a cytokine, a second nucleic acid sequence encoding a LAP which is the latency associated peptide (LAP) of TGFβ-1, -2, -3, -4 or -5 wherein a nucleic acid sequence encoding an aggrecanase proteolytic cleavage site which is DVQEFRGVTAVIR (SEQ ID NO: 24) is provided between the first and second nucleic acid sequences.

8. A cell comprising a vector of claim 6.

9. A composition comprising a nucleic acid construct as claimed in claim 5.

10. A kit of parts comprising a fusion protein as claimed in claim 1 and an administration vehicle.

11. A process for preparing the fusion protein as claimed in claim 1, comprising production of the fusion protein recombinantly by expression in a host cell and purification of the expressed fusion protein.

12. A process for preparing a nucleic acid construct as claimed in claim 5 comprising ligating together nucleic acid sequences encoding the LAP, the aggrecanase cleavage site, and the cytokine, optionally including a linker sequence on either side of the aggrecanase cleavage site.

13. A cell comprising a nucleic acid construct as claimed in claim 5.

14. A composition comprising a cell as claimed in claim 8.

15. A kit of parts comprising a nucleic acid construct as claimed in claim 5 and an administration vehicle.

16. A kit of parts comprising a cell as claimed in claim 8 and an administration vehicle.

* * * * *